(12) United States Patent
Gervais et al.

(10) Patent No.: US 10,380,376 B2
(45) Date of Patent: Aug. 13, 2019

(54) SYSTEM AND METHOD FOR PROTECTING AND CONTROLLING ACCESS TO ANALYTICAL RESULTS OF A DIAGNOSTIC TEST ASSAY

(71) Applicant: One Drop Diagnostics Sàrl, Neuchâtel (CH)

(72) Inventors: Luc Gervais, Neuchâtel (CH); Jörg Ziegler, Grenchen (CH)

(73) Assignee: ONE DROP DIAGNOSTICS SÀRL, Neuchatel (CH)

( * ) Notice: Subject to any disclaimer, the term of this patent is extended or adjusted under 35 U.S.C. 154(b) by 0 days.

(21) Appl. No.: 15/029,579

(22) PCT Filed: Oct. 15, 2014

(86) PCT No.: PCT/EP2014/072156
§ 371 (c)(1),
(2) Date: Apr. 14, 2016

(87) PCT Pub. No.: WO2015/055738
PCT Pub. Date: Apr. 23, 2015

(65) Prior Publication Data
US 2016/0267295 A1 Sep. 15, 2016

(30) Foreign Application Priority Data
Oct. 15, 2013 (EP) .................................... 13188787

(51) Int. Cl.
*H04L 29/06* (2006.01)
*G06F 21/62* (2013.01)
(Continued)

(52) U.S. Cl.
CPC .......... *G06F 21/6245* (2013.01); *G06F 19/00* (2013.01); *G16H 10/40* (2018.01); *G06F 2221/2107* (2013.01); *Y02A 90/26* (2018.01)

(58) Field of Classification Search
CPC .................................................. G06F 21/6245
See application file for complete search history.

(56) References Cited

U.S. PATENT DOCUMENTS

| 4,020,830 A | 5/1977 | Johnson et al. |
| 4,945,045 A | 7/1990 | Forrest et al. |

(Continued)

FOREIGN PATENT DOCUMENTS

| CN | 101246529 A | 8/2008 |
| CN | 103164605 A * | 6/2013 |

(Continued)

*Primary Examiner* — Shawnchoy Rahman
(74) *Attorney, Agent, or Firm* — Pauley Erickson & Kottis

(57) ABSTRACT

A reader unit (31) is configured to be operationally coupled with an assay unit (11) that is capable of performing one or more diagnostic tests (13) on one or more physiological samples (15), and is configured (32, 36) to obtain test raw data (73) of diagnostic tests performed on an assay unit operationally coupled with the reader unit. The reader unit comprises an encryption module (33) that is configured to encrypt input data with locking key data (75), the input data comprising the test raw data, or data derived from said test raw data. The reader unit is configured to provide access to the encrypted data (77), but not to the input data.

19 Claims, 20 Drawing Sheets

(51) Int. Cl.
*G16H 10/40* (2018.01)
*G06F 19/00* (2018.01)

(56) References Cited

U.S. PATENT DOCUMENTS

| | | |
|---|---|---|
| 5,641,640 A | 6/1997 | Hanning |
| 5,719,324 A | 2/1998 | Thundat et al. |
| 6,018,713 A | 1/2000 | Coli et al. |
| 7,039,810 B1 | 5/2006 | Nichols |
| 7,162,451 B2 | 1/2007 | Berger et al. |
| 2002/0161606 A1 | 10/2002 | Bennett et al. |
| 2004/0181528 A1 | 9/2004 | Tirinato et al. |
| 2005/0055240 A1 | 3/2005 | Walsh et al. |
| 2005/0065890 A1 | 3/2005 | Benaloh |
| 2012/0023592 A1* | 1/2012 | Wilson ............... G06F 19/323 726/28 |
| 2012/0029303 A1 | 2/2012 | Shaya |
| 2012/0232367 A1* | 9/2012 | Allegri ............... A61B 5/145 600/365 |
| 2013/0024382 A1* | 1/2013 | Dala ............... G06F 19/322 705/51 |
| 2013/0079599 A1* | 3/2013 | Holmes ............... G06F 19/3418 600/300 |
| 2014/0350955 A1* | 11/2014 | Yedidsion ........... G06F 19/3418 705/2 |
| 2016/0012249 A1* | 1/2016 | Keppler ............... G06F 21/602 726/28 |

FOREIGN PATENT DOCUMENTS

| | | |
|---|---|---|
| EP | 1 776 919 A1 | 4/2007 |
| WO | WO 89/09938 A1 | 10/1989 |
| WO | WO 99/22236 A1 | 5/1999 |
| WO | WO 02/01271 A1 | 1/2002 |
| WO | WO 02/48701 A2 | 1/2002 |
| WO | WO 02/100261 A2 | 12/2002 |
| WO | WO 2008/094837 A1 | 8/2008 |

* cited by examiner (a)

| BACK | ORDER |
|---|---|
| Cardiac Markers | ■ |
| Troponin T | ■ |
| Myoglobin | ■ |
| CK-MB | ■ |
| BNP | ■ |
| D-Dimer | ■ |
| Sexually Transmitted Disease | ☐ |
| Electrolytes and Chemistries | ■ |
| Drug Screening | ☐ |
| Virology | ☑ |
| Hematology | ■ |
| Inflammation Markers | ⊟ |
| Interleukin-6 (IL-6) | ☐ |
| C-reactive protein (CRP) | ☑ |
| Procalcitonin (PCT) | ☐ |
| Acute-phase serum amyloid A | ☐ |

Fig. 16

| Database of Test Data | | | |
|---|---|---|---|
| ID | Chip Spec. ▲ | Test Date | User Nar |
| 15... | Panel 1 | 2012/2/2, 20:02 | Barbara Mi |
| 15... | Panel 1 | 2012/2/3, 8:45 | Barbara Mi |
| 15... | Panel 1 | 2012/2/3, 13:15 | Barbara Mi |
| 15... | Panel 1 | 2012/2/3, 19:57 | Barbara Mi |
| 15... | Panel 1 | 2012/2/17, 13:07 | Barbara Mi |
| 15... | Panel 1 | 2012/5/9, 21:14 | Barbara Mi |
| 15... | Panel 1 | 2012/10/1, 10:20 | Barbara Mi |
| 58... | Panel 2 | 2012/1/29, 9:23 | Barbara Mi |
| 58... | Panel 2 | 2012/2/3, 13:28 | Barbara Mi |
| 58... | Panel 2 | 2012/8/13, 15:43 | Barbara Mi |
| 23... | Panel 3 | 2012/1/29, 15:30 | Barbara Mi |
| 23... | Panel 3 | 2012/2/3, 13:00 | Barbara Mi |
| 31... | Panel 3 | 2012/12/10, 23:48 | Barbara Mi |

SYSTEM AND METHOD FOR PROTECTING AND CONTROLLING ACCESS TO ANALYTICAL RESULTS OF A DIAGNOSTIC TEST ASSAY

FIELD OF THE INVENTION

The invention relates to diagnostic systems for obtaining and handling analytical result data from assay units, reader units, diagnostic devices, and diagnostic kits for such diagnostic systems, and methods for controlling access to analytical results.

BACKGROUND OF THE INVENTION

Today, physiological samples such as for example body fluids may be analyzed for a wide variety of biochemical analytes. Accurate medical diagnostics is an important part of medical treatment such as the identification of health conditions and disease, monitoring, prognosis, and companion diagnostics. There are two main settings in which medical diagnostics systems are used: dedicated medical laboratories and the so-called point-of-care (PoC) testing.

The term "physiological sample" in the context of this description shall comprise all liquid, solid or gaseous material that is either biological material obtained from the patient, such as blood, urine, stool, or tissue, or samples that are prepared for subsequent analysis based on such biological material.

Laboratory diagnostic devices as used in medical laboratories generally provide a wide variety of analytical capabilities. For example, devices sold by Illumina and Affymetrix provide molecular diagnostics of deoxyribonucleic acid (DNA) and ribonucleic acid (RNA). Clinical analysers, such as those sold by Roche and Abbott, provide tests for immunochemistry (antibody based detection) and clinical chemistry (detection of small chemical molecules). Devices as sold for example by Beckman Coulter can count cells in body fluids.

Such diagnostic devices are sensitive, accurate and flexible, and provide a high throughput. However, they also have the disadvantage of being expensive, and requiring well trained personnel for operation. For this reason such diagnostic devices are mainly used in hospital laboratories and centralized medical laboratories, where they can be used most efficiently. However, since such devices require a physiological sample from a patient, said samples have to be transported to the medical laboratory, where the analysis is going to be performed. As a result, the results of the analysis are available only after hours or even days.

An increasingly large number of diagnostic tests are carried out at the point of care, close to the patient, for example in a medical practice, an emergency room of a hospital, an ambulance vehicle, or even at the patient's side. Point-of-care diagnostic devices are often portable, and capable of obtaining analytical results rapidly (within minutes). Their use is generally much simpler, so that the diagnostic tests can be carried out by ordinary medical personnel or even the patient himself.

The most widespread point-of-care diagnostic devices perform lateral flow immunoassay strip tests. Such tests are available for a wide variety of diagnostic indications such as pregnancy, HIV, malaria, influenza testing. Corresponding devices are provided from a multitude of manufacturers, such as e.g. Swiss Precision Diagnostics, Alere, Bayer, and Siemens. The lateral flow test is usually limited to the detection of one or two analytes and qualitative detection, for example a clear colour change.

The Alere Triage MeterPro system is an immunochemistry system composed of an assay unit in the form of a consumable cartridge and an evaluation device in the form of a reusable bench-top reader. Cartridges are available to detect panels of biomarkers such as a three-protein cardiac panel (Myoglobin, CK-MB and Troponin I), and a drug-screening panel. Thus such a cartridge allows the simultaneous testing of a sample for three analytes. Every new panel of biomarkers requires a new test cartridge. The Alere epoc system and Abott i-STAT system have cartridges that may measure panels of blood gases, electrolytes, and metabolites. For the Abott i-STAT system, cartridges are available that measure single cardiac biomarkers (Troponin I, CK-MB, or BNP). These devices are sensitive and accurate. A main limitation is the high price per tested analyte, compared to laboratory diagnostic machines. Another disadvantage is the limited variety of available test cartridges.

New biosensor systems allow multiplexed detection of a large number of analytes for point-of-care diagnostic applications. Such devices offer advanced and integrated analytical capabilities, rivalling those of laboratory diagnostic devices.

The Gyros Lab-on-a-CD system and the Advanced Liquid Logic digital microfluidic system are capable of detecting over 100 analytes at a time, using a bench-top analyser. Other biosensing approaches for detecting various biochemical analytes are provided for example in U.S. Pat. No. 5,719,324, WO2002/048701, U.S. Pat. No. 4,020,830, WO89/009938, U.S. Pat. Nos. 4,945,045, and 5,641,640.

Medical diagnostics devices typically consist of a reusable measuring device and a consumable component (test unit or reagents). A user wishing to carry out a certain diagnostic test will select a diagnostics device having the required analytical capabilities. For example, a diabetes mellitus patient wanting to know the glucose concentration in his blood, may use a dedicated diagnostic system comprising a reusable blood glucose meter and a consumable blood glucose test strip.

If an evaluation device allows to perform different diagnostic tests, the user will have to choose the corresponding consumable assay unit. For example, a user wanting to test for myocardial infarction may use an Alere Triage meter (evaluation device) and a Cardio 3 Panel cartridge (assay unit) to test for three cardiac biomarkers. A user wanting to test for other analytes such as further cardiac biomarkers, will have to select other test cartridges that can perform the required diagnostic tests.

The costs for the consumable assay units are not primarily defined by the mere actual production costs, but on one side by the R&D costs to be recovered by the manufacturer, and on the other side by the health insurance reimbursement tariffs applicable on a certain diagnostic test for a certain analyte, which generally differ between countries and/or insurance companies, etc. Thus the purchasing price for a certain assay unit will depend on the analytical capabilities, such as the number and the kind of analytes that can measured by the consumable assay unit.

Such an approach of recovering costs via the purchasing price of the assay unit works for consumable assay units capable of measuring one analyte, or a few analytes.

Combinations of analytes are available only for tests that are routinely needed together, such combined tests for cardiac biomarkers or drug abuse screenings. Thus, generally only few different diagnostic combination tests are available.

The purchase prize approach does not provide an optimal solution for diagnostic systems providing extended multiplexing capabilities, as discussed above, when used for point-of-care diagnostics, with reusable evaluation device and consumable assay unit. For example, the application of a diagnostic system that can test for a hundred analytes at the same time would be cost prohibitive, since the purchase prize would depend on the R&D costs and the reimbursement tariffs of said hundred analyte tests, although the manufacturing costs of the consumable assay unit are comparable to assay units with much less diagnostic capabilities.

Medical diagnostics systems are increasingly integrated in data communication networks, allowing the exchange of data between hospitals, medical practices, centralized laboratories, the patient's home, and even mobile units such as ambulance vehicles or rescue helicopters. Medical diagnostics systems capable of communicating with electronic health care management systems further provide a variety of benefits for ordering, billing, calibrating, and synchronizing test results with electronic health records. In all such applications, however, confidentiality of sensitive private medical data is an issue.

US2002/0161606, US2005/0055240 and U.S. Pat. No. 6,018,713 describe systems for ordering diagnostic tests from centralized clinical laboratories. Said systems are based on a client terminal and a remote server in a centralized laboratory. The user enters patient information, selects and orders diagnostic tests to be carried out by the centralized laboratory. Reports on the results of the diagnostic tests can be sent to the client terminal. The performed tests can be automatically charged to a health insurance company. Although having certain logistical advantages, the disclosed systems still have the common problem of centralized laboratories, namely the necessity of samples having to be transported to the laboratory, in order to carry out the diagnostic tests.

EP1776919 discloses a subscription-based biosensor monitoring system. The system allows biosensor measurements to be conducted using a reusable meter device and consumable test strips only when a subscription is active. The meter device communicates its identifier code and ROM circuit identifier code to a remote server, which verifies that the subscription is active, and enables the meter device to conduct the diagnostic tests.

WO99/022236 proposes a cellular network based calibration method for blood glucose test strips. A meter device that is coupled to a mobile telephone measures the result of the diagnostic test performed on the test strip, and communicates the results and an identification code of the test strip to a remote server. The remote server transmits the calibration data associated to the test strip to the mobile telephone, which then calculates the final test results. The disclosed system does not protect the privacy of test results.

US2004/0181528 shows an inventory management system for point-of-care devices. The electronic system tracks a plurality of point-of-care diagnostics devices in regard to their expiry date, consumption time, room temperature storage time, and manages the ordering of additional devices to replenish inventory. The disclosed system is limited to inventory management, and the replenishment of inventory when diagnostic devices are no longer useable.

WO02/100261 describes a system for point-of-care in-vitro blood analysis. The system is based on a modified smart card that can conduct biosensing tests. The smart card is inserted into a smart card reader, which measures an analog output signal, converts the analog signal to a digital signal, and sends said digital raw data to a general purpose computer device to produce analytical results. The disclosed system is limited to modified smartcard based biosensors, and can only produce analytical results with the help of a general purpose computer.

The unauthorized or fraudulent access to sensitive personal health care data, which includes analytical results, is a major safety and privacy concern.

US 2012/0029303 A1 discloses a virtual medical examination system comprising a remote patient device, and a diagnostic device, which can communicate wirelessly, by wire, or via a network. The diagnostic device, e.g. a camera, generates diagnostic results, e.g. pictures, and transmits said result data to the remote patient device, which encrypts the data and transmits the encrypted data to a patient record server. The medical personnel using the diagnostic device have access to the diagnostic data. The purpose of the system is to provide real-time remote virtual medical examination.

In U.S. Pat. No. 7,039,810 B1, one or more implanted medical devices communicate wirelessly with a local computer ("programmer") that allows to program the implanted medical device. The programmer provides an encrypted data connection to a remote expert data centre.

US 2005/065890 A1 discloses a method to securely distribute media content such as movies, for example for media players in airplanes, or via set top boxes, and the like. In one embodiment, media content data (e.g. a movie) are encrypted with a content key. This content key is again encrypted with a public key of a specific media player, for each authorized media player. The multitude of encrypted content keys for all media players are distributed together with the encrypted content data. Each authorized media player can decrypt the content key previously encrypted with its own specific public key, but cannot decrypt the other encrypted content keys. This allows to securely distribute an identical, protected media content data set to a large number of authorized receivers, without the need of producing individually secured data carriers for each receiver, and without the need of contacting a remote authorization server. In another variant, the media content data are split up in a number of data partitions. Of each partition, two or more copies are provided, each partition copy having a unique fingerprint. All those partitions are encrypted with a different content key. For each authorized media player, a unique combination of partitions representing the complete media content is provided, and the corresponding individual content key set is encrypted with the public key of the authorized media player. The encrypted media content is distributed together with all encrypted content key sets of all authorized media players. Once decrypted, the complete media content data set has a unique fingerprint. As a result, illegal copies of the content can be traced back to a specific media player. In all disclosed variants, identical protected content is distributed and made accessible to a multitude of predefined authorized recipients. Neither the content to be made accessible, nor the list of recipients can be changed in the process.

WO 02/01271 A1 discloses a method for selectively encrypting and decrypting different sections of an electronic document, which allows to provide selective access levels to groups of authorized users to different sections of the document. Users in a group with a certain access level know the private key of this level, and can access those sections of a document that have been previously encrypted with the corresponding public key of this certain access level. Sections of different access level may also be convoluted. Thus, of a section with a first access level, a certain subsection with a second access level is encrypted with a second public key, and then the complete section including the encrypted subsection is encrypted with the first public key. The assignment between the different sections of encrypted content and the user groups corresponding to a certain access level is static.

There is a general need for diagnostics systems that allow the cost efficient use of multiplexed diagnostic tests for point-of-care applications, so that the advantages of such multiplexed diagnostic tests can be fully exploited.

OBJECTS OF THE INVENTION

It is an overall objective of this invention to provide advantageous diagnostic systems and diagnostic devices, as well as methods to protect the results of diagnostic tests, and to control the access to said data, that overcome one or more of the above-mentioned and other problems.

It is a further object of the invention to provide advantageous reader units and assay units for use in such diagnostic systems and devices according to the invention.

Particularly, a diagnostic system according to the invention should allow the use of medical diagnostics technologies with multiplexed diagnostic test capabilities for point-of-care applications, without the user being forced to receive all results of all diagnostic tests. Advantageously, the user should be able to choose in advance, during, and/or after the test which analytical results the user actually wants to receive.

Furthermore, the diagnostic systems and data protection and access control methods according to the invention should allow flexible payment or subscription models for diagnostic tests.

Another object of the invention is the simplified distribution and inventory management of consumable assay units, an improved and extended quality control of the manufacturer, as well as an improved safety level for the user.

Diagnostic systems and access control methods according to the invention should ensure confidentiality of patient data at all time.

These and other objects are substantially achieved by a diagnostic system, a diagnostic device, a reader unit, a diagnostic kit, and a method according to the independent claims. Further advantageous embodiments follow from the dependent claims and the description.

SUMMARY OF THE INVENTION

According to the present invention, the above-mentioned objects are particularly achieved by a diagnostic system that is capable to perform one or more diagnostic tests on one or more physiological samples, to measure the outcome of the diagnostic tests, and to generate corresponding digital measurement raw data, to subsequently process said raw data, maybe with the help of auxiliary data (e.g. calibration data of the sensor) to analytical result data (for example a concentration of a certain analyte in the blood serum), to encrypt said result data to make them reversibly inaccessible to a user (the data are locked), and to selectively enable access to parts or all of said encrypted result data, after appropriate authorization of the user.

In the context of this description, the terms, "encrypted data, "locked data" and "protected data" are to be understood as essentially synonymous, since data locked by encryption with a certain encryption key are protected against unlocking/access by an unauthorized person that does not know the decryption key.

The authorization level of a user corresponds to the diagnostic tests for which the user is authorized to access the analytical results. The decrypted, unlocked analytical result data can then be used for the intended medical purposes. A diagnostic system according to the invention thus gives a user not the choice which diagnostic tests are carried out, but the choice which analytical results of said tests he actually wishes to know, or to get access to, respectively. A particular advantage is the fact that the decision of a user is not final. He may later wish to unlock further results. Once access to those results has been acquired, this is possible without any negative consequences to the quality of the analytical results: All analytical results have been obtained and stored as protected data in the first place, while the generally transient results of the assay unit have a restricted life time during which they can be reliably read from the assay unit.

Alternatively to processing the measurement raw data to analytical result data prior to encryption, the measurement raw data may be encrypted directly, so that the processing to the analytical result data is only possible after subsequent decryption of the raw data.

The miniaturized features of a diagnostic chip or similar multiplexed diagnostic test assay devices may integrate a large number of reagents and sensors. The addition of more analytical capabilities to a diagnostic chip, by integrating additional reagents and sensors, results in minimal marginal costs. Thus, a user of such a diagnostic system may purchase an assay unit with such a diagnostic chip for a minimal up-front price, and may purchase only the needed analytical results, thereby eliminating the need of additional diagnostics chips, and reducing the total test costs. The purchase price may thus depend on the purchased analytical results, and not on the costs for the assay units themselves.

It should be noted that the assay unit may also be realized such that it can only carry out one diagnostic test on one physiological sample, or one type of diagnostic tests on a multitude of physiological samples from different patients. In such a case, however, some advantages of the inventive diagnostic system may not be fully exploitable, while others are.

Furthermore it may be useful to have single diagnostic test assay units to ensure compatibility for diagnostic systems with a broad range of offered assay units, or for simplification of the payment process for very expensive diagnostic tests.

In a particularly advantageous embodiment, a reader unit according to the invention may be realized such that it is also capable of reading out the results of older type of assay units, thereby ensuring backward compatibility.

The user is enabled to access certain analytical results either by being provided with the necessary means to decrypt and thus unlock the corresponding encrypted data sets, for example by providing the key data necessary for decryption, or by having the corresponding encrypted data decrypted in a secure realm of the diagnostic system, and delivering the now unlocked, useable analytical result data to the user. The other, still encrypted data sets, even if known to the user, remain protected, since the information content is inaccessible and locked for the user.

Since all diagnostic tests have actually been carried out, the unlocked analytical results may be stored for further use in the form of the encrypted data sets, and access may be enabled at any time in the future. Thus the diagnostic system according to the invention offers the possibility to enable certain diagnostic tests even at a later point in time. For example certain diagnostic tests may only become relevant when the results of already enabled diagnostic tests suggest a certain possible diagnosis that has to be further investigated.

It even becomes possible to distribute assay units without any authorization means, in which case the purchase prize may be chosen very low, since essentially it has only to cover basic manufacture and distribution costs. The authorization means can then be distributed separately.

Such an approach also reduces the potential financial loss of the owner of an assay unit due to the expiration of maximum-shelf time. Since less different types of assay unit are needed, the overall number of assay units to be kept in stock can be decreased, which furthermore reduces the money bound in hardware.

The term "user" or "user realm" in the context of this description does not only mean the human person, for example a patient or medical personnel, operating the diagnostic device according to the invention. These terms also include all parts of the diagnostic system that are under factual control of the user, for example an auxiliary computer device such as a laptop computer, a tablet computer, or a smart phone, that is at least temporarily part of the diagnostic system according to the invention. Thus data in the user realm of the diagnostic systems principally have to be considered to be known to the user, and are only protected from unauthorised use if locked and encrypted with a key that is unknown to the user.

A "secure part" or "secure realm" of the diagnostic system according to the invention is the part or parts of the diagnostic system that are not fully and unrestrictedly accessible by the user. For example all electronic parts that are involved in handling the yet unencrypted measurement raw data and analytical result data, and involved in the subsequent encryption of the measurement data, can be realized in a tamper-proof manner. Getting unauthorized access to data within the secure realm of said tamper-proof electronic parts is only possible with considerable time and effort, and malevolent dedication.

The protection of such electronic parts may be achieved by different means, including the mechanical protection of electronic circuits, for example by embedding them in synthetic resin, or by especially designing the circuits in a tamper-proof manner. Corresponding technologies and approaches are known from the prior art, particularly in the context of electronic retail payment systems and the like.

Following from the basic inventive principle of the invention of splitting up the diagnostic test process in i) carrying out the diagnostic tests, and ii) making the diagnostic results accessible, it is possible to use assay units that are capable of performing a large number of different diagnostic tests on a single sample, without the need to actually sell said assay unit for a purchase prize that would be appropriate for an assay unit with such capabilities. Since the user will only get access to the results of the certain group of diagnostic tests for which he is authorized, the other diagnostic tests, although in fact having been actually performed, are negligible in regard to the purchase prize of the assay unit, since they are locked and inaccessible to the user.

In a diagnostic system according to the invention, an assay unit can be used that is, for example, capable of simultaneously analyzing a blood sample of a patient in regard to 100 different biomarkers. However, the assay unit may be distributed together with authorization means that enable only access to the analytical results of three specific biomarkers, for example Myoglobin, CK-MB and Troponin I, which are relevant for the diagnosis of myocardial infarction. Thus the purchase prize is defined by these three diagnostic tests, and can be defined much lower than it would be necessary if all analytical results would be available to the user, as in the prior art.

The very same type of assay unit may also be sold with authorization means for another panel of biomarkers, or for single biomarkers only. The only difference is the authorization means, thus the kind of diagnostic tests for which the user is pre-authorized, and the analytical results of which become accessible to the user.

Since less types of different assay units are necessary, the units as such can be produced in much larger numbers than it would be possible when several different assay units would have to be produced. The resulting lower manufacture costs also compensate any additional manufacture costs for adding more different tests to the assay unit.

A diagnostic system according to the invention can be realized as an integrated single device, or as a system with two or more separate units or devices that are operationally coupled, at least during use, for example by electronic interfaces, data connections, etc. Some units and parts of the diagnostic system may also be remotely located.

In a particular advantageous variant of the invention, a diagnostic system according to the invention comprises one or more assay units that are capable of performing one or more diagnostic tests on the one or more physiological samples, and a reusable reader unit, to which the assay unit(s) can be operationally coupled, and which is capable to read out the diagnostic test signals or measurement raw data from the assay unit(s).

The assay unit is advantageously provided as a consumable part that can be used only once, and is disposed after use. Thus particularly all elements that come, or might come, into contact with physiological sample material, are advantageously part of the disposable assay unit.

The reader unit, on the other hand, is advantageously a reusable device comprising the more expensive electronic parts, and/or other parts that can be used more than once without negative influence on the quality of the diagnostic tests.

The reader unit may also read further data that are provided on the assay unit, for example stored on a memory chip, or a one- or two-dimensional bar-code. Such data may also include alphanumeric data that are read by the user, and manually entered into reader unit with corresponding interface means, e.g. a keyboard. Instead of providing the further data on the assay unit itself, part or all of said data may also be provided on the package in which the assay unit is packed, or an accompanying data carrier such as a printed card or paper, a chip card, or the like.

The data carrier of the assay unit can be implemented using authentication integrated circuits containing non-volatile memory for data and key storage. The authentication can be based for example on a host-slave system using challenge response messages. Such integrated circuits are available from several manufacturers such as Atmel, NXP, Maxim, Texas Instruments. Authentication integrated circuits provide strong and affordable cryptographic security using standard-based algorithms.

Said further data may comprise auxiliary data such as calibration data necessary for evaluating the results of the diagnostic tests, batch numbers, assay unit type, time-stamps, unique assay unit identifiers, etc. Said further data may further comprise authorization data that will enable a user to access part or all of the analytical result data.

The reader unit is configured to prevent access to the measurement raw data, or the analytical results data obtained from the measurement raw data, by encrypting the data.

Optionally part or all of the further data may also be encrypted, or may remain in plain-text.

At least the reader unit must belong to the secure realm of the diagnostic system, such that only encrypted analytical result data are obtainable from outside, for example via an electronic interface.

Optionally it is also possible to secure the functional connection between assay unit and reader unit, such that it is not possible for a malevolent user to circumvent the protection mechanisms according to the invention, by directly accessing the assay unit, which may be particularly relevant when the connection is an electronic interface. In such a case, also the assay unit belongs to the secure realm.

The encrypted data are then provided to an evaluation unit of the diagnostic system, which is operationally coupled to the reader unit. The evaluation unit belongs to the user realm of the diagnostic system, and advantageously performs the data handling, including making certain protected and locked data accessible to the user. The evaluation unit may for example be realized as a standard computer device, on which software is provided that allows to carry out the necessary tasks, utilizing the already present hardware of the computer device, such as CPU, memory and data storage means, electronic interfaces, display, keyboard, etc.

In order to provide an additional level of security, the software that enables the evaluation device to carry out its task is advantageously only operative if a reader unit, and/or an assay unit, is connected to the evaluation unit. Thus the reader unit or the assay unit may act as a hardware key, a so-called dongle. Alternatively the necessary software, or essential parts of it, may not be stored on the evaluation unit itself, but on a memory module of the reader unit, or the assay unit. For example, the reader unit or the assay unit may comprise a dedicated flash memory unit, which may appear as a storage volume when connected to the evaluation unit, on which the software is stored.

Providing certain software elements on the assay unit has the additional advantage that new types of assay units may bring with them the necessary software elements, so that no manual software update of the evaluation unit, or the reader unit, is necessary.

Data can be transferred from the reader unit to the evaluation via a suitable data interface, for e.g. a bus interface, such as USB, RS232, etc., an optical fibre connection, or a wireless communication link, such as Bluetooth, WLAN, IR interface, or another suitable data link.

The data transfer may also occur manually, for example by temporarily storing the data on portable memory devices (e.g. smart card, flash memory devices and cards, writable CDROM), that are subsequently functionally connected to the evaluation unit.

The evaluation unit, e.g. the computer device, is provided with means that allow to perform various tasks, such as managing the encrypted data, obtaining authorization data, decrypting the data based on available authorization means, to process data to analytical results, to communicate with remote systems, to store data etc.

An evaluation unit will carry out at least part of the tasks and functions of the diagnostic system that can take place in the public realm without compromising the security of the locked analytical results. Since no special or unusual hardware is needed for those task and functions, including data processing, the use of an ordinary computer device for those tasks has the advantage that the overall hardware costs can be decreased, since either a computer device is already available to the user, or can be acquired for comparably low costs.

The reader unit of a diagnostic system according to the invention, on the other hand, advantageously comprises only the minimum hardware and software that is necessary to obtain the measurement raw data or analytical result data from the assay unit, and to protect said data by encryption.

In other embodiments according to the invention, the functions of the reader unit, as well as part or all of the functions of the evaluation unit, are integrated in one single diagnostic device.

Alternatively an integrated diagnostic device may be provided in which the assay unit and the reader unit are not separable. This may be particularly advantageous when the diagnostic test setup and the corresponding read-out electronics are deeply integrated in the detection technology, and may not be easily realized as a separate reusable part.

The question if assay unit, reader unit, and/or evaluation unit are realized as separate units or are partially combined in integrated devices, however, is not primarily relevant for the invention. If such integration is favourable or not mainly depends on the involved diagnostic test technology, as well as the costs involved. For an assay unit with considerably high manufacturing costs, it may be simply irrelevant from an economical point of view whether some parts of the electronics, or even the complete electronics including the encryption and or data processing electronics, are part of the consumable assay unit. Furthermore it has to be assumed that in the future electronic parts will become even less expensive, more energy efficient, and smaller, all of which favours integrated approaches.

The evaluation unit may simply be located at the place of the reader unit. However, the necessary data connection may also be established over a longer distance, for example a communication network. Thus the evaluation unit may be located in a different room, or may be even farer away.

The authorization means necessary for getting access to the protected and locked results of the enabled diagnostic tests may be provided in the form of authorization data stored in a memory chip, or as a one-dimensional or two-dimensional barcode printed, or even as an alphanumerical code printed on the assay unit that has to be entered manually into the evaluation device. Advantageously the authorization data are unique, and function only for a specific assay unit entity, which will prevent possible misuse of authorization means.

The authorization means may be provided directly on the assay unit, or on a separate unit, for example an accompanying smart card comprising the authorization data, or simply a piece of paper with a printed barcode or an alphanumerical code.

The protection of the analytical results is important, in order to control access to the results of the diagnostic tests, and to prevent fraudulent actions. In an advantageous approach, the reader unit and the assay unit communicate with the means of a host controller and a secure authenticator. The host controller of the reader unit sends a challenge to the secure authenticator of the assay unit, and receives a response. This response is evaluated by the reader unit to establish authenticity of the assay unit. Such methods are known to the skilled person, and can be implemented using authentication integrated circuits containing non-volatile memory for data and key storage. The authentication can be based for example on a host-slave system using challenge response messages. Such integrated circuits are available from several manufacturers, as already explained further above.

If the reader unit identifies the assay unit as authentic, the assay unit transfers an encrypted rule, stored in a memory module of the assay unit, to a secure memory module in the reader unit. The secure memory comprises a private key that allows to decrypt the encrypted rule, in order to retrieve a matching rule. Once the matching rule has been obtained, the individual measurement raw data are assigned to the individual diagnostic tests, and the analytical results of the assay unit are compiled. The analytical result data set is then encrypted and finally provided in this protected and locked form to the user. All these steps are carried out in the secure realm of the reader unit, for example in a dedicated tamper-proof electronic circuit.

In one variant, said matching rule comprises a list of test element identifiers and their corresponding analyte identifiers, which is required to match the multitude of obtained raw data to the specific diagnostic tests that have been carried out in parallel. In other words, the matching rule is required to convert the measured raw data of the test elements to a list of analytical results. For example, in the case of an optically detected assay unit with test elements for a multitude of analytes arranged in a matrix, the matching rule allows to know which test element corresponds to which detected analyte.

Advantageously, the matching rule is provided on the assay unit in such an encrypted form that groups of assay units, or individual assay units, with identical matching rule comprise different encrypted rules. This may be achieved e.g. by reversibly altering the data set of the matching rule prior to encryption, for example by rearranging the data according to a certain rule. The result will be different encrypted rule data sets for identical matching rules.

In a more advantageous variant, the matching rule and/or encrypted rule is changed over time. For example, a new set of test element positions, resulting in a new matching rule, can be generated for every new batch of assay units. Alternatively, or in addition, the matching rule may be converted into different encrypted rules (see above) for every batch, or even for every individual assay unit. The corresponding encrypted rule is stored e.g. in a memory module of the assay unit. The most consequent approach would be to generate a new matching rule for every newly fabricated assay unit.

In an alternative variant, the matching rule stored on the assay unit correspond to an identifier of a database record, with the database stored in a secure memory of the reader unit. The database record comprises the necessary information to match the raw data to the analytical results they represent. The database record may for example comprise the matching list of test element identifiers and their corresponding analyte identifiers. This method has the advantage of minimising the amount of memory required on the data carrier of the assay unit, and relegating the memory requirements to the reader unit. Yet another alternative would be to store the database in a secure remote database, transmitting the database record to the reader unit over a secure channel.

In yet another embodiment, the database records may be provided in encrypted form. In addition to an identifier of the appropriate database record, the matching rule then comprises a decryption key that allows to decrypt the corresponding database record.

In a further embodiment, the encrypted rule can be embedded directly in the arrangement of test elements. Certain test elements can be used as a data carrier to store the encrypted rule, instead of being used for diagnostic test purposes. The reader unit measuring the raw data would then read these test elements and obtain the encrypted rule.

A benefit of such a protection method is that the analytical results are protected and can only be modified by an authorised user. Another benefit is that only authentic assay units can be used to obtain correct raw data and corresponding analytical results. Yet another benefit is that only authentic reader units are used to obtain correct raw data and corresponding analytical results. Only approved authentic readers and assay units are used to the maximum of their capabilities in providing rapid, accurate, precise, sensitive, large dynamic range analytical results.

While a nefarious user could try to decipher the matching rule of an assay unit, such a task would require a large amount of identical assay units, and would be extremely time consuming, non-obvious, and cost prohibitive. The fact that the matching rule and test element positions would regularly change, and that a user cannot recognize which assay units comprise the identical matching rule, would make this task virtually impossible.

In order to allow purchasing analytical results, or more precisely purchasing access to already existing, but protected analytical results, the tamper-proof reader unit can be equipped with an electronic credit unit memory, which can be refilled by temporarily connecting and synchronizing the reader unit with a remote payment clearing server. For purchasing analytical results, the counter of the credit memory is decreased by a corresponding amount of credit units. This embodiment has the advantage that no online access is necessary, except for the short time period of reloading the credit memory with credit units. Instead of a credit memory that has to be reloaded prior to use, and thus is based on a pre-payment model, it is also possible to record the spent credit units, and to regularly synchronize the credit balance with the remote payment clearing server, which then may issue an invoice or charge an account for the used credit units. Such approaches can also be combined.

In another advantageous embodiment of the invention, instead of completely integrating the authorization means into the assay unit, it is also possible to realize the authorization means in combination with a remote authorization server. In this embodiment the evaluation unit requires access, at least temporarily, to the remote authorization server. The necessary authorization data to unlock access to the enabled analytical result data are then provided to the user by the remote authorization server.

In one advantageous variant of the invention, the reader unit encrypts the test measurement raw data, or the analytical result data, respectively, with a symmetric encryption algorithm.

Symmetric encryption algorithms, also known as secret key encryption, are based on a shared secret key known only to the involved communication partners, wherein the same key is used for encryption and decryption. Examples are AES, Blowfish, CAST5, DES, IDEA, RC2, RC4, RC6, Serpent, Triple DES, Twofish, etc. Instead of using an encryption algorithm, a binary key of equal length as the data to be encrypted may be added mod 2 to the data. Such an approach requires longer keys as encryption algorithms, but is more secure and faster. Since the data sets to be encrypted are not particularly long, the keys are also not particularly long.

In order to allow at a later stage the selective unlocking of certain analytical results, the different data sets $D_1, D_2, \ldots D_n$, corresponding to the different analytical results of the diagnostic tests $T_1, T_2, \ldots T_n$, are individually encrypted with different keys $A_1, A_2, \ldots A_n$. Preferably the keys are random keys for one-time use, which are generated just prior to use, and not used a second time. Prior to encryption the data sets $D_1, D_2, \ldots D_n$ may optionally be expanded with additional meta data, the meta data comprising other useful data such as diagnostic test number, assay unit ID, reader unit ID etc. The encrypted data $AD_1$, $AD_2$, ... $AD_n$, are transferred from the reader unit to the evaluation unit, and are stored there for later use.

The secret keys $A_1, A_2, \ldots A_n$ may also be combined with additional meta data to expanded key data sets $A^*_1$, $A^*_2, \ldots A^*_n$ the meta data comprising other useful data such as diagnostic test number, assay unit ID, reader unit ID etc. The expanded key data sets are then encrypted a second time, with an asymmetric encryption algorithm, also known as public key encryption.

Examples for such asymmetric encryption algorithms are RSA, Diffie-Hellman, Digital Signature Algorithm, ElGamal, ECDSA, XTR. In such an asymmetric encryption, a private key B that is known only to the receiver enables the receiver to decrypt data, while a public key C associated to the private key B is made available to potential communication partner that want to send data, and allows them to encrypt data, but not to decrypt them. For larger data sets to be encrypted, asymmetric encryption may be combined with symmetric encryption, by encrypting the data with a secret key (advantageously a random key for one-time use) and a symmetric encryption algorithm, and subsequently encrypting the secret key itself with the public key and an asymmetric encryption algorithm. The encrypted secret key may then be transmitted together with the encrypted data set.

In the inventive diagnostic system, the public key should advantageously be provided already stored in the secure realm, such as the assay unit, or the reader unit, in order to avoid the risk of tampering by providing a faked public key from outside.

After encryption with public key C, the encrypted key data $CA^*_1$, $CA^*_2$, ... $CA^*_n$ are transferred to the remote authorization server. Advantageously the encrypted key data are stored in the reader unit, or more advantageously in the evaluation unit, where they can be stored together with the corresponding encrypted data $AD_1$, $AD_2$, ... $AD_n$. Alternatively to sending all encrypted key data, only the keys that belong to the required analytical results may be sent to the remote authorisation server.

On the remote authorization server, the key data are temporarily stored. The user may then unlock one or more diagnostic tests, for example tests $T_2$, $T_7$, and $T_{34}$, by purchasing the authorization means for accessing the analytical results of said diagnostic tests, for example by credit card payment, by charging an account, by issuing an invoice, by converting a prepaid voucher, etc. Corresponding remote electronic payment technologies are well known to the skilled person. In the case an assay unit has been pre-enabled for certain diagnostic tests, corresponding unique identification means, such as the assay unit ID, will allow the remote server to obtain the necessary authorization data information from a local database.

Once the payment transaction has been properly concluded, or authorization information for the assay unit ID has been retrieved from a database, the authorization server decrypts the enabled encrypted key data $CA^*_2$, $CA^*_7$, $CA^*_{34}$ with private key B. The decrypted keys $A^*_2$, $A^*_7$, $A^*_{34}$, corresponding to the required diagnostic tests, and then sent back to the evaluation unit, where the keys are used to decrypt the enabled encrypted data $AD_2$, $AD_7$, $AD_{34}$ to accessible analytical results $D_2$, $D_7$, $D_{34}$.

The above-mentioned variant of the invention has the advantage that no result data are transferred to the remote server, but only key data without information content, such that fraudulent access to sensitive patient data or the like on the remote server is impossible.

In another variant of the invention, the reader unit encrypts the test measurement raw or diagnostic result data D directly with the asymmetric encryption algorithm, using public key C, and transfers the encrypted data CD to the remote server, where they are decrypted after establishing authorization, and returned as accessible data D to the evaluation unit. Advantageously in such a solution the data connection between diagnostic device and remote authorization server is encrypted, in order to ensure data secrecy in regard to outside parties that may monitor communication networks.

In order to ensure data secrecy in such a case even in regard to the remote authorization server, the analytical result data D can be encrypted by the reader unit with an additional secret user key E that is not known to the remote authorization server. These encrypted data ED are encrypted with the public key C, and these double encrypted data CED are transmitted to the remote authorization server. The secret user key E can be based on a password chosen by the user, or a one-time random key generated by the reader unit and provided to the user.

The remote authorization server will be able to decrypt with its private key B one level of the encryption of the data set, and will then return the still encrypted data ED to the user. However, the remote authorization server system itself cannot access the data ED, since the key E is not available to the remote authorization server. Data privacy is therefore ensured even if a third party obtains unauthorized or fraudulent access to the remote server. Once the data ED are returned to the evaluation unit, the user can remove the second level of encryption with secret key E. The diagnostic test results D are finally accessible to the user.

Transferring the complete data to the remote authorization server provides the additional advantage that the results may be remotely stored, in order to ensure continued availability in the future, and as a backup solution.

As has been already briefly discussed above, for embodiments of the invention in which access is enabled via a remote authorization server, the distribution of assay units that are pre-enabled for a certain diagnostic test, or a panel of certain diagnostic tests, is particularly advantageous. Instead of storing the necessary access data on each single assay unit, or providing each assay unit with an additional carrier of such authorization data, the corresponding unique assay unit IDs are recorded during manufacture, and the authorization data for the pre-enabled diagnostic tests are stored in a local database. The authorization procedure then consists of transferring the assay unit ID, together with the encrypted key data or encrypted analytical result data, from the evaluation unit to the remote authorization server, decrypting the keys or analytical results of the pre-enabled diagnostic tests, and returning the decrypted data to the user.

In a particularly advantageous embodiment of the invention, different levels of authorization may be implemented. A first level of authorization may for example provide only access to the information if a certain analytical result lies within a certain defined value range. A user interface may then emphasize the diagnostic tests for which the analytical results lie within the range, or outside, respectively, This may for example give an indication for a potentially problematic health condition. In case the user wishes to further inspect certain results, he may then purchase a second level of authorization, which provides full access to the analytical results. This variant of the invention may be especially useful for quickly scanning through multiple analytes and check the overall health condition of a patient.

A further advantage of diagnostic systems according to the invention is given by the fact that in case certain batches of assay units, or parts of their included tests, are later found to be potentially prone to erroneous results, for example due to a production problem, a recall procedure can be organized via the remote authorization server. For example, the authorization procedure may be set up in such a way that prior to carrying out the diagnostic tests, the assay unit must be pre-registered with the authorization unit, for example by transmitting the assay unit ID. In case the corresponding ID belongs to a set of assay units that has been recalled, a warning message is provided to the user, requesting not to use the assay unit and to return it to the manufacturer.

The same procedure may be used to prevent the use of assay units that have reached their maximum life-time, or to prevent an accidental second use of an assay unit. If the diagnostic tests have been carried out despite the previous warnings, appropriate measures can be taken, depending on the severity of the problem. Either access to the analytical results may be refused, or the results may be accompanied by warning messages, the receipt of which has to be acknowledged by the user.

Another advantage is the possible prevention of counterfeit assay units. Assay units that do not originate from an approved manufacturer may not fulfil the necessary quality standards. However, it may be difficult for a user to recognize such unapproved products, and a manufacturer may be at risk to be held liable for products that he did not produce. Since all approved assay units can be registered during manufacture, unapproved assay units can be easily identified.

Another advantage of the invention is that analytical results can be shared over a network, for example within a hospital, and accessed by remote authorized users. Analytical results may then be accessed, selected, viewed, or purchased from a dedicated evaluation unit, for example in the patient's room, or from an authorized remote access device, for example on a computing device in the office of the responsible physician. By encrypting analytical results after they are measured, it is possible to protect the privacy of the patient's personal data.

In a variant of such an approach, an evaluation unit may store the protected, locked data received from the reader unit, and/or the unlocked analytical result data, on a remote storage server. Such a remote storage server may be a dedicated server operated for a certain user or group of users. Alternatively, the remote storage server may be realized in combination with the remote authorization server, which is operated by a third party. In the latter case, the remote storage server may advantageously store the already unlocked data for all diagnostic tests, although optionally the data may be encrypted with a secret key of the user.

Such a variant is particularly advantageous because the appropriate long-time data storage including backup can be ensured, and the analytical data may more conveniently be accessed by remote access devices, such as a computer in a doctor's office, be it for review of already present result data, or for purchasing access to further analytical results.

In yet a further embodiment of a diagnostic system according to the invention, which does not need a connection to a remote server for purchasing additional analytical results, a tamper-proof authorization unit such as a smartcard device comprises a private key B, and a pre-loaded credit unit counter. The authorization unit is operationally connected to the reader unit, or to the evaluation unit, for example in the case of a smart card with a standard smart card reader, or may be temporarily or permanently integrated into the assay unit. The reader unit will use the public key C corresponding to the private key B stored on the authorization device, to encrypt the result data D with the public key C, either indirectly or directly, similar to the approaches discussed above for a remote authorization server. Thus either encrypted data AD and encrypted secret keys CA are provided to the evaluation unit, or encrypted data CD. When a user wants to purchase or view analytical results, the encrypted keys CA, or the encrypted data CD, respectively, are transmitted to the authorization device, together with information on the requested diagnostic test results. The authorization device decreases the credit unit counter accordingly, decrypts the data with private key B, and returns the decrypted data A or D to the evaluation unit.

In a further variant of such an embodiment, the reader unit encrypts analytical results using one of a set of public keys, and provides them to the evaluation unit. The set of private keys corresponding to the reader unit public keys are stored on the tamper-proof authorization device. When a user wants to purchase or view analytical results, the evaluation unit requests the corresponding private key necessary for decrypting the data from the authorization device. The authorization decrements the credit unit counter, and provides the requested private key. Each pair of public/private keys must only be used once. The evaluation unit then decrypts the analytical results using the private key and provides the analytical results to the user.

The correspondence between the pairs of public keys and private keys proves the authenticity of the authorization device itself. While the private key set must already be present on the authorization unit, the public key set is either provided already together with the assay unit, or is downloaded from a trusted remote server based on a unique identifier of the authorization device, or is provided on a pre-installed local database. The latter two possibilities are particularly advantageous, because in the first case the authorization device does only function in combination with a certain assay unit.

Another variant of this embodiment is to use fine-grained access control encryption, with a single public key and a separate private key for each analytical result. The private keys are stored on the authorization device, and the public key is stored on the reader unit. In this example, analytical results may be encrypted using the public key in the reader unit, and certain analytical results may be subsequently decrypted using the private keys in the smartcard. There are several techniques used for fine-grained access control. One such technique is attribute based encryption.

In yet another variant, the encrypted analytical results are transferred from the reader unit to the authorization device, where they are securely stored.

In yet a further embodiment, a secret key is provided to a reader unit, and/or evaluation unit, and/or remote server. The reader unit will encrypt the analytical result data using the secret key. When a user wants to purchase or view analytical results, the evaluation unit may use the secret key to decrypt the analytical results and provide them to the user. The encrypted analytical results may be transmitted from the reader unit to a remote storage server, and a remote access device, each having the secret key. Although simple, this method is only secure as long as the secret key is kept hidden and inaccessible to the user. This embodiment further requires that the manufacturer provides the secret key on the reader unit, the evaluation unit, etc. Alternatively, the secret key may be transmitted using standard secure data transfer techniques from the reader unit to the server and other remote access devices.

In another variant of the invention, sensor data are selectively read out from the assay unit. A user may select the desired analytical results. The reader unit may readout only the data from the sensors required to obtain the selected analytical results. This variant may be useful when a user knows before a diagnostics test which analytical results are needed. However, the variant may have the disadvantage that some sensor data is not read and therefore some potential analytical results are irreversibly discarded.

The present invention may comprise one or more of the features recited in the attached claims, and/or one or more of the following features and combinations thereof.

An advantageous embodiment of a reader unit according to the invention is configured to be operationally coupled with an assay unit that is capable of performing one or more diagnostic tests on one or more physiological samples, and is configured to obtain test raw data of diagnostic tests performed on an assay unit operationally coupled with the reader unit. The reader unit comprises a data protection module that is configured to obtain and temporarily store the test raw data, to convert said test raw data into analytical result data, to encrypt said analytical result data with locking key data to encrypted data, and to provide said encrypted data on an output interface. The protection module is a tamper-proof module that is configured to prevent access to data stored in the module. Thus, the protection module, and the reader unit as a whole, provide access to the encrypted data, but not to the analytical result data.

Advantageously, the protection module comprises an encryption module for carrying out the encryption.

In another advantageous variant of said previous embodiments of a reader unit according to the invention, the reader unit is configured to receive auxiliary data from a second data interface.

In a further advantageous variant of said previous embodiments of a reader unit according to the invention, the protection module is configured to encrypt the locking key data with second level key data to encrypted locking key data, and to provide said encrypted locking key data on the output interface. Thus, the protection module, and the reader unit as a whole, provide access to the encrypted locking key data, but not to the locking key data.

In yet another advantageous variant of said previous embodiments of a reader unit according to the invention, the reader unit is configured to provide data on the first data interface.

An advantageous embodiment of diagnostic device according to the invention comprises a reader unit according to the invention as described above, and an assay unit capable of performing one or more diagnostic tests on one or more physiological samples. The assay unit and the reader unit are permanently or releasably operationally coupled to each other, and the reader unit is configured to obtain test raw data of diagnostic tests performed on the assay unit. Alternatively or in addition the diagnostic device comprises an evaluation unit, the evaluation unit and the reader unit being permanently or releasably operationally coupled to each other, and the evaluation unit being configured to receive data from the reader unit, to decrypt at least parts of said data, using authorization key data, and to use the decrypted output data for obtaining analytical result data.

In an advantageous variant of such a diagnostic device according to the invention, the evaluation unit comprises a data processing module that is configured to decrypt encrypted data.

In another advantageous variant of said diagnostic devices according to the invention, the evaluation unit comprises a data output module, for example a display or a printer; and/or a data input module, for example a keyboard or a track pad; and/or a combined data input/output module, for example a touch screen.

An advantageous embodiment of a diagnostic system according to the invention comprises one or more reader units according to the invention as discussed above; one or more assay units capable of performing one or more diagnostic tests on one or more physiological samples, the assay units being configured to be operationally coupled to the reader units, and the reader units being configured to obtain test raw data of diagnostic tests performed on the assay units; and one or more evaluation units, configured to be operationally coupled to the reader units, to receive data from the reader units, to decrypt at least parts of said data, using authorization key data, and to use the decrypted output data for obtaining analytical result data.

Advantageously, the evaluation unit comprises a data processing module that is configured to decrypt encrypted data.

The evaluation unit can comprise a data output module, for example a display or a printer; and/or a data input module, for example a keyboard or a track pad; and/or a combined data input/output module, for example a touch screen.

In one advantageous variant of a diagnostic system according to the invention, one or more authorization units are operationally coupled to an evaluation unit, and/or one or more remote authorization servers are connected to the evaluation unit via a communication network. The authorization units and/or remote authorization servers are configured to provide, upon fulfillment of certain conditions, the authorization key data to the evaluation unit.

In one advantageous variant of a diagnostic system according to the invention, one or more authorization units are operationally coupled to an evaluation unit, and/or one or more remote authorization servers are connected to the evaluation unit via a communication network. The authorization units and/or remote authorization servers are configured to receive encrypted data from the evaluation unit, to decrypt parts or all of the encrypted data upon fulfillment of certain conditions, and to provide the decrypted data to the evaluation unit.

In both said variants of a diagnostic system according to the invention, the certain conditions that must be fulfilled is the provision of certain authorization data to the authorization units, and/or the remote authorization servers.

A diagnostic kit according to the invention comprises one or more assay units with a test module capable of performing one or more diagnostic tests on one or more physiological samples, and a reader unit according to the invention as discussed above.

An advantageous variant of a method according to the invention for controlling access of a user to a subset of data for which the user is authorized, out of a complete data set, particularly for controlling access of the user to analytical results of an multiplex assay unit, comprises the steps: I) providing the complete data set; II) encrypting the complete data set with locking key data; III) providing the encrypted data set to the user; and IV) providing the user with authorization means that enable the user to get access to that part of the encrypted data set that corresponds to the subset of data for which the user is authorized, but not to the other part of the encrypted data set.

In a particularly advantageous variant of said method for controlling access of a user to analytical results of an assay unit, the method comprises the steps: a) providing an assay unit that is configured to carry out in parallel multiple diagnostic tests on one or more physiological samples; b) reading out from said assay unit a complete data set of analytical results of said multiple diagnostic tests; c) encrypting the complete data set of analytical results with locking key data; d) providing the encrypted complete data set of analytical results to the user; and e) providing the user with authorization means that enable the user to get access to a certain authorized subset of the complete data set of analytical results as present in the encrypted complete data set of analytical results, but not to the other part of the complete data set of analytical results.

In one advantageous variant of such a method according to the invention, the authorization means are authorization key data that allow to decrypt certain parts of the encrypted data, namely the encrypted complete data set of analytical results, such that the decrypted data correspond to the authorized subset of data, namely the certain authorized subset of the complete data set of analytical results.

In another advantageous variant of such a method according to the invention, the authorization means are authorization data that enable the user to receive authorization key data from an authorization unit, or from a remote authorization server, wherein the authorization key data allow to decrypt certain parts of the encrypted data, namely the encrypted complete data set of analytical results, such that the decrypted data correspond to the authorized subset of data, namely the certain authorized subset of the complete data set of analytical results.

Advantageously, in said methods according to the invention, in step II)/step c) different subsets of the data set, namely different subsets of the complete data set of analytical results, are encrypted with different locking keys, which together form the locking key data, to different subsets of encrypted data, which together form the encrypted data, namely the encrypted complete data set of analytical results.

Encryption in step II)/step c) can take place with an asymmetric encryption algorithm, and the locking keys can be public keys for the asymmetric encryption algorithm.

In a particularly advantageous variant of this method with asymmetric encryption, the authorization means are private keys of the asymmetric encryption algorithm, which together form the authorization key data, wherein said private keys allow to decrypt those subsets of encrypted data, namely those subsets of the encrypted complete data set of analytical results, of which the decrypted data subsets correspond to the authorized subset of data, namely the certain authorized subset of the complete data set of analytical results.

Alternatively, encryption in step II)/step c) can take place with a symmetric encryption algorithm, and the locking keys can be secret keys for the symmetric encryption algorithm.

In one particularly advantageous variant of this method with symmetric encryption, the authorization means are certain keys of the locking key data, which together form the authorization key data, wherein said certain keys allow to decrypt those subsets of encrypted data, namely those subsets of the encrypted complete data set of analytical results, of which the decrypted data subsets correspond to the authorized subset of data, namely the certain authorized subset of the complete data set of analytical results.

In another particular advantageous variant of this method with symmetric encryption, after step II)/step c) the locking key data are encrypted with an asymmetric encryption algorithm, using one or more public keys for the asymmetric encryption algorithm, which together form second level key data, to encrypted locking key data.

In such a variant of the method, that the encrypted locking key data can be provided to the user. Alternatively or in addition, the encrypted locking key data can be provided to an authorization unit, or to a remote authorization server, and the authorization means can be authorization data that enable the user to command the authorization unit, or the remote authorization server, to decrypt certain parts of the encrypted locking key data, such that the decrypted locking key data correspond to those locking keys that allow to decrypt the subsets of encrypted data of which the decrypted data subsets correspond to the authorized subset of data, and to provide the decrypted locking key data to the user.

In yet another advantageous variant of the basic method according to the invention as described above, the encrypted data, namely the encrypted complete data set of analytical results, are provided to an authorization unit, or to a remote authorization server. The authorization means are authorization data that enable the user to command the authorization unit, or the remote authorization server, to decrypt certain parts of the encrypted data, such that the decrypted data correspond to the authorized subset of data, namely to the certain authorized subset (73a, 74a) of the complete data set (73, 74) of analytical results, and to provide the decrypted data to the user. In a particular advantageous variant, prior to encryption in step II)/step c), the different subsets of the data set are encrypted with privacy key data, which are provided to the user.

In the methods according to the invention as discussed above, the complete data set that is encrypted in step II)/step c) comprises the analytical results data of an assay unit, or alternatively the test raw data of an assay unit. The authorized subset of data comprises the authorized analytical results, or alternatively those authorized test raw data that can be further processed to the authorized analytical results.

In the methods according to the invention as discussed above, the authorization means are provided on the assay unit, or on a data carrier associated to the assay unit.

BRIEF DESCRIPTION OF THE DRAWINGS

In order to facilitate a fuller understanding of the present invention, reference is now made to the appended drawings. These references should not be construed as limiting the present invention, but are intended to be exemplary only.

FIG. 12 is a schematic view of an illustrative interface for selecting, purchasing and viewing analytical results.

FIG. 16 is a schematic view of an illustrative interface for a database of analytical result data that allows to retrospectively purchase or view analytical results.

DESCRIPTION OF EMBODIMENTS OF THE INVENTION

Certain aspects of embodiments disclosed herein by way of example are summarized below. It should be understood that these aspects are presented merely to provide the reader with a brief summary of certain forms that any implementation disclosed and/or claimed herein might take, and that these aspects are not intended to limit the scope of the present disclosure. Indeed, any implementation disclosed and/or claimed herein may encompass a variety of aspects that may not be set forth below.

Components that are identical, or that are identical at least in terms of their function, are designated below by identical or at least comparable reference numbers.

Figure 1:
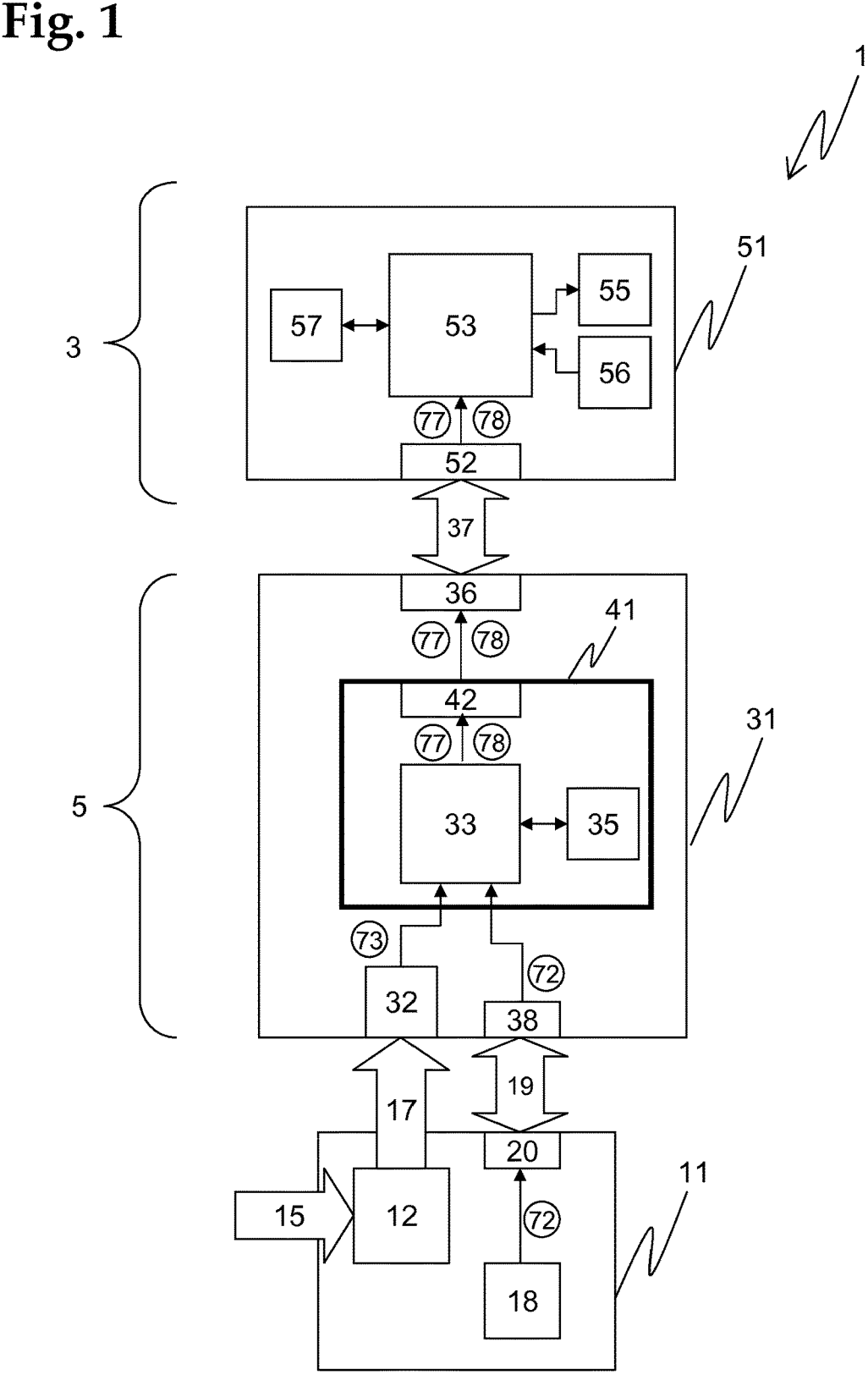
FIG. 1 is a schematic view of an advantageous embodiment of a diagnostic system according to the invention, with an assay unit, a reader unit, and an evaluation unit.

An advantageous embodiment of a diagnostic system 1 according to the invention is schematically shown in FIG. 1, comprising an assay unit 11, a reader unit 31, and an evaluation unit 51, which are functionally coupled.

The assay unit 11, which is advantageously realized as a consumable unit, comprises a test module 12 that is capable of carrying out one or more diagnostic tests on a provided physiological sample 15. A memory module 18 allows to store different additional data 72 that do not contain analytical results, such as auxiliary data regarding the assay unit, e.g. assay unit ID number, lot number, manufacturing date, expiry date, assay unit type, other specifications, calibration data, encrypted matching rule, and the like. Furthermore said data 72 may comprise authorization data, for example for enabling the access to a set of diagnostic tests for which the assay unit is pre-authorized, thus without the need for separate purchasing said analytical results. In addition the data 72 may also comprise data that are specific for the carried out diagnostic tests, but do not contain the results as such, for example time stamps, error messages, protocols, patient data, etc.

The data 72 on the memory module 18 can be accessed by the reader unit, via a data connection 19 established by coupled data interfaces 20, 38 of the assay unit and the reader unit. The data connection can be realized as a parallel or serial data bus, e.g. USB, or Ethernet. Other possibilities include also wireless access means such as near-field rf communication, such as RFID technology and the like, or rf protocols such as Bluetooth/IEEE-802.15, WLAN/IEEE-802.11 etc., but also optical communication means, for example IR data transfer interfaces etc.

The memory module 18 can be realized by any state of the art technology that allows to permanently or transiently store digital data, for example a flash memory chip. The reader unit may have full access to the data stored on the memory module, or access may advantageously be controlled by the memory module itself, which may for example be realized as a "smart card" chip.

Depending on the type of technology on which the assay unit is based, the diagnostic tests are carried out before the assay unit is releasably connected to the reader unit, such that the coupling is only needed for the mere result read-out. This may be advantageous when diagnostic tests require a substantial time period, or have to be carried out in a special environment, or several assay units run diagnostic tests in parallel. In other cases it may be more advantageous to carry out the diagnostic tests while the assay unit is connected to the reader unit.

The reader unit may also have auxiliary functions such as supplying power for the assay unit, or providing a data interface for a control unit (not shown), or a control module that may for example be integrated in the reader unit 31, or the evaluation unit 51, and which allows to control the operations of the assay unit 11.

When the assay unit 11 is releasably operationally coupled to the reader unit 31, a sensor module 32 of the reader unit will allow the reader unit to read out the outcome 17 of the diagnostic tests. For example, the sensor module may measure test signals, such as for example an analog voltage signal of an electrode pair, or the optical information as it is visible for an optical receiver (e.g a camera) of the sensor module 32. The sensor signals are then converted to test raw data 73 in digital form. An analog voltage signal 17 may for example be converted by an AD converter into a digital output value, which represents the test raw data. Test raw data may also be the digital data that can be read from a CCD chip, etc.

Figure 2:
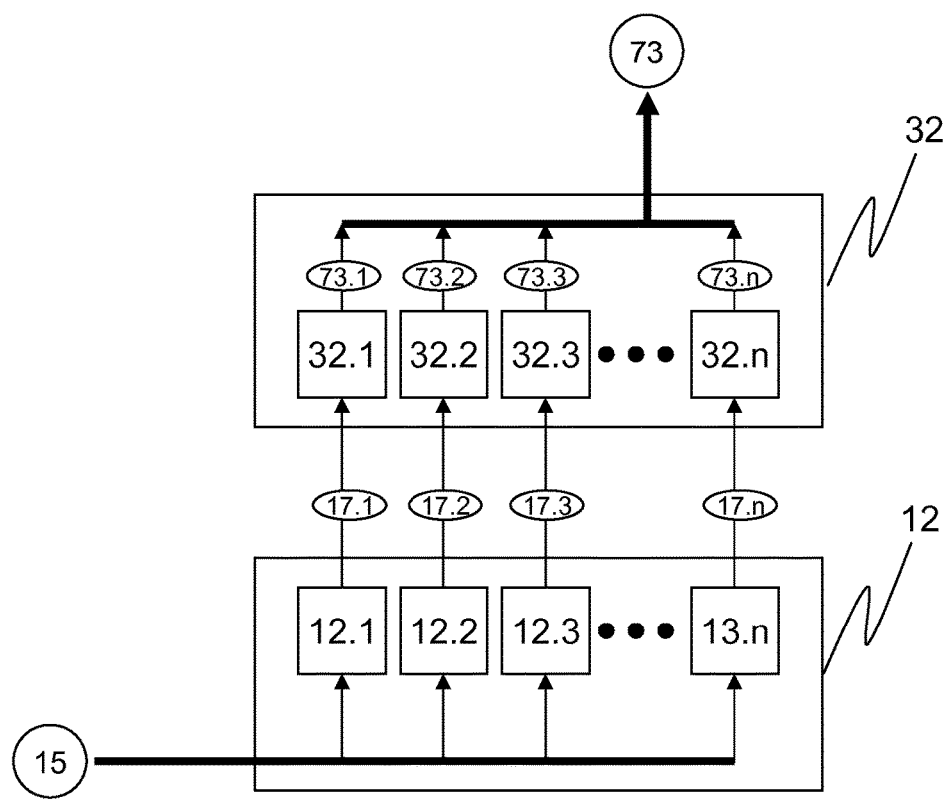
FIG. 2 is a schematic view of the read-out of test result data in the embodiment of a diagnostic system as shown in FIG. 1.

A possible approach of the read-out of test result data in the embodiment of a diagnostic system as shown in FIG. 1 is schematically shown in FIG. 2. The physiological sample 15 is provided to a number of test elements 12.1, ..., 12.$n$ of the test module, wherein each element is capable of carrying out one specific diagnostic test. The output signals 17.1 ..., 17.$n$ of the test elements are then measured by sensor elements 32.1, ..., 32.$n$ of the sensor module 32, each providing a single set of raw data 73.1, ..., 73.$n$ of the corresponding diagnostic tests. All sets of raw data together form the test raw data 73.

Assay units that can be used in the inventive diagnostic system can be realized in a variety of technologies that are known from the prior art, such as for example test strips, microscope slides, microfluidic chips, microchips, cartridges, compact discs, multi well plates etc. The assay units may contain different test elements that are capable of measuring a variety of analytes. The analytes may for example be proteins, nucleic acids, cells, small molecules, gases, electrolytes, or pathogens (e.g. bacteria, virus, prions) etc. Depending on the applied diagnostic technology, the assay unit may also comprise different reagents, auxiliary systems, micro-pumps, microprocessors, etc that are necessary to carry out the diagnostic tests. The kind of diagnostic technology as such, however, is not relevant for the inventive principle, as long as the assay unit is able to provide the diagnostic test results in a form that can be read out by a suitable sensor module of a reader unit, and converted in digital form. A variety of transduction mechanisms can be used, such as optical, mechanical, electrical, or chemical means.

The terms test element, test module, sensor module, and test raw data have to be understood in a broad sense. For example, in a case where an assay unit is based on a test strip technology, where the amount of analyte corresponds to a certain colour of a particular array on a test strip, the optical information of the test strip is detected by an optical sensor or sensor module, and is converted into test raw data in digital form. In the case of a more complex assay unit with integrated sensors, said sensors may provide analog electrical signals to multiple electric contacts of a multi pin plug. The sensor module measures said signals, and generates corresponding digital test raw data. More complex assay units may comprise data processing capabilities themselves, and directly provide test raw data to the reader unit.

Instead of fully parallel detection, it is also possible to measure the signals $17.1, \ldots, 17.n$ sequentially, with only one or a few sensor elements. A digital camera as a sensor element may also receive a picture of all test elements at the same time, the digital picture forming the test raw data 73, in which case the distinct test raw data $17.1, \ldots$ are defined by the position of the corresponding test element in the picture. It may also be possible to carry out the diagnostic tests in sequential order. The only condition that must be fulfilled, in order to carry out the invention, is that the results of the different test elements $12.1, \ldots, 12.n$ must be clearly separable from the overall test raw data 73, or alternatively it must be possible to derive the distinct analytical results $74.1, \ldots 74.n$ from the overall test raw data 73 by suitable data processing. Obviously in the case of an assay unit intended to carry out only one single diagnostic test, this condition is always met.

The reader unit 31 comprises a tamper-proof protection module 41 that obtains the test raw data 73 and the additional data 72. The protection module comprises an encryption module 33, which is able to encrypt the test raw data 73 as explained in detail further above, in order to lock the data and make them inaccessible to the user, or the evaluation unit, respectively. Certain data that do not require encryption may be forwarded by the encryption module as plain-text data 78.

An optional volatile and/or non-volatile memory module 35 is connected to the encryption module, and allows to temporarily store data. It is also possible to integrate memory capabilities directly into the encryption module.

The encryption module 33 can be realized as an integrated circuit in which all functions are hardwired, or as a microprocessor on which a program is carried out that may be provided stored on the memory module, or a combination of both.

The encryption module may also be used to convert test raw data into analytical result data, or a separate conversion module may be used (not shown).

Encrypted data 77 and plain-text data 78 data are provided on an output interface 42 of the tamper-proof module 41, from which they can be received and be sent to the evaluation unit 51 of the diagnostic device, via a data interface 36 of the reader unit 31, a data connection 37, and a data interface 52 of the evaluation unit. For this data connection, the same possibilities are available as for the data connection 19 between assay unit 11 and reader unit 31, as discussed further above.

The reader unit 31 belongs to the secure realm 5 of the diagnostic system 1 according to the invention. In other words, the user or any other outside person is not intended to have access to any data inside the reader unit that are not explicitly provided to the user. The reader unit 31, or at least the protection module 41, is realized in a tamper-proof manner. Thus a user or any third party should not be able to access data that are not intended to be accessible, namely the yet unencrypted test raw data or analytical results data, prior to encryption. There are several techniques and approaches known in the prior art for protecting electronic circuits from unauthorized access or manipulation.

The evaluation unit 51 of the diagnostic system 1 comprises a data processing module 53 that is capable of performing the different tasks that have to be carried out in order to get access to the authorized analytical results data, to subsequently evaluate said data, and to finally provide usable results to the user. Advantageously the data processing module is a microprocessor, or a CPU, capable of carrying out corresponding program code.

The evaluation unit 51 belongs to the user realm 3 of the diagnostic system, which means that the user has principally access to any data present on the evaluation unit.

The evaluation unit 51 may comprise a data output module 55 that allows to present information to a user. The data output module may for example be realized as a display, a built-in printer unit, or simply a number of LEDs providing status information. Furthermore the evaluation unit may comprise a data input module 56 that allows a user to manually enter data, or to give instructions to the evaluation unit. The data input module may for example comprise a number of keys or buttons, or a complete keyboard, data output module and input module may also be combined, e.g. in the form of a touch screen.

The evaluation unit may be a special device dedicated for the use in a diagnostic system according to the invention. However, since essentially all necessary and optional hardware elements of the evaluation unit are available in standard computing devices, such as desktop personal computers, laptop computers, tablets, smart phones, etc., the evaluation unit is advantageously realized with such a computing device, equipped with suitable software for carrying out the various tasks. It may also be possible to realize the evaluation unit by two or more coupled devices, for example a basic evaluation unit dedicated for the use in the diagnostic system, and an additional computer device connected to the basic unit, that allows for example remote control of the basic unit, or increases the possibilities of the unit.

A typical course of actions and events as it may take place in a diagnostic system according to the invention is schematically explained in the flowcharts in FIGS. 3, 3A, 4, and 5.

In a step S11, the user chooses an appropriate assay unit and carries out the diagnostics tests on a physiological sample, following the prescribed protocol. The assay unit is then coupled S12 to the reader unit, and the output signal of the assay unit test elements is measured S13. The resulting test raw data are read out S14, and processed to analytical results for all diagnostic tests S15. In a next step S16 the analytical results are then locked by encryption, and thus protected from access by the user. The encrypted data are stored S17, either on the reader unit, or the evaluation unit. The system is now in state A.

Figure 3:
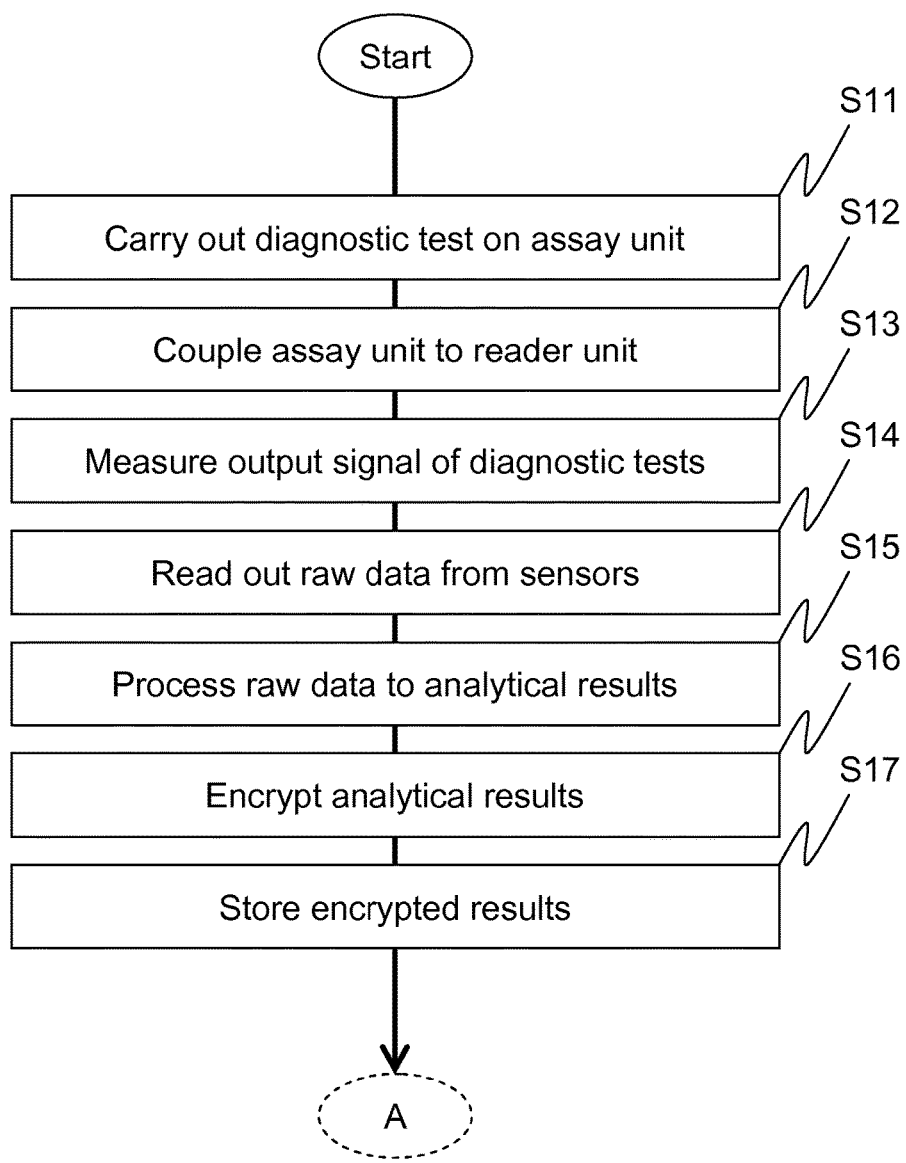
FIG. 3 is a flowchart describing the part of the process in which the diagnostic tests are carried out, the results are measured and processed, subsequently locked by encryption, and the protected results provided to the user for potential further use.
Figure 3A:
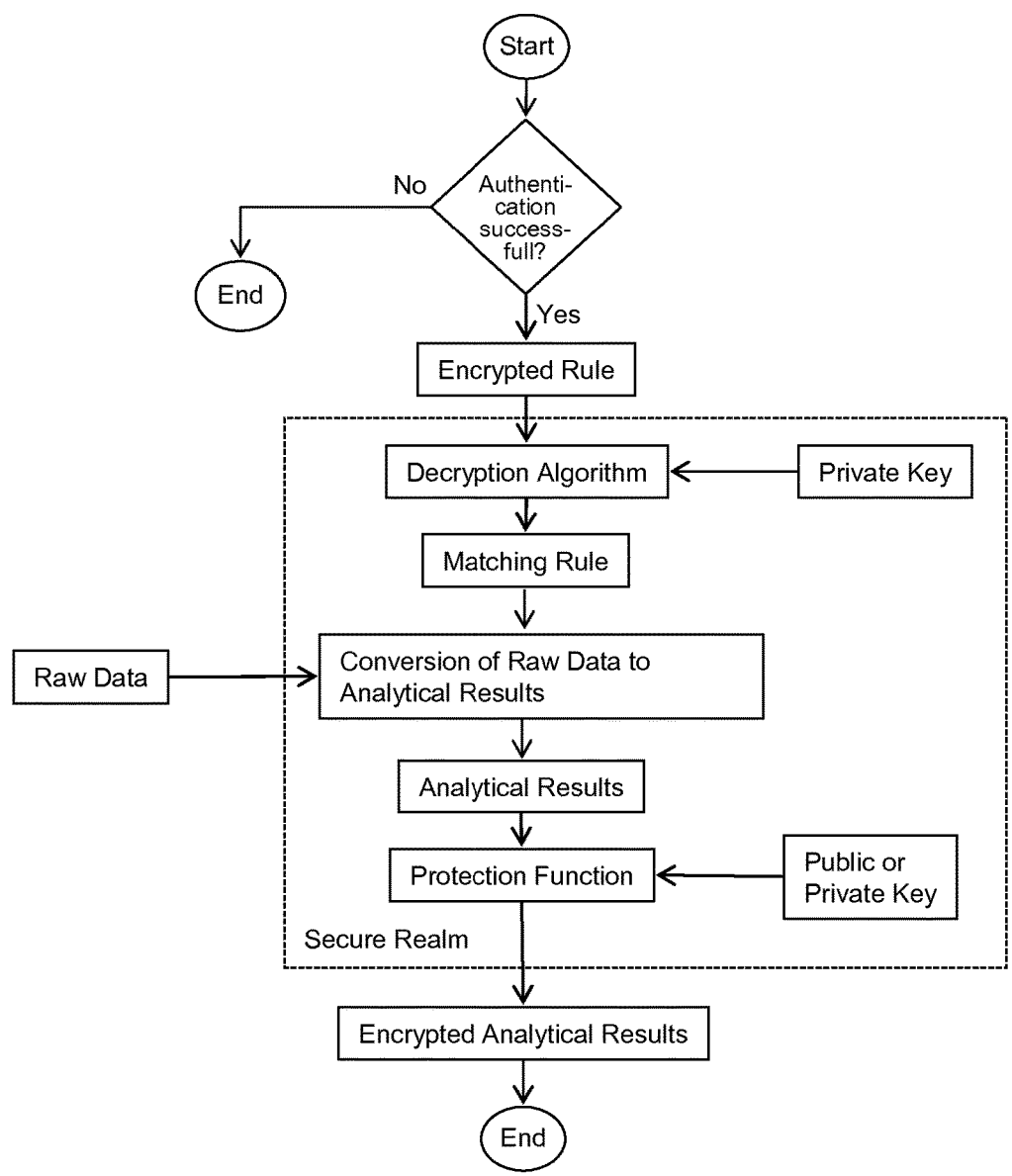
FIG. 3A is a flowchart describing an advantageous variant of processing the raw data to the analytical results (step S15).
Figure 4:
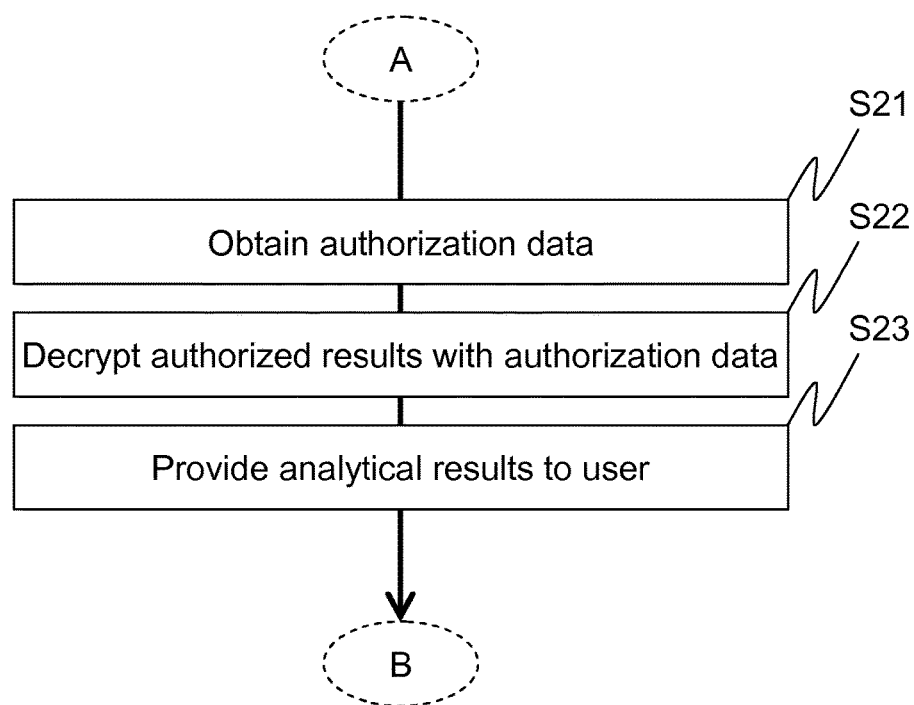
FIG. 4 is a flowchart describing the part of the process in which access to the locked, protected results is enabled for pre-authorized diagnostic tests.
Figure 5:
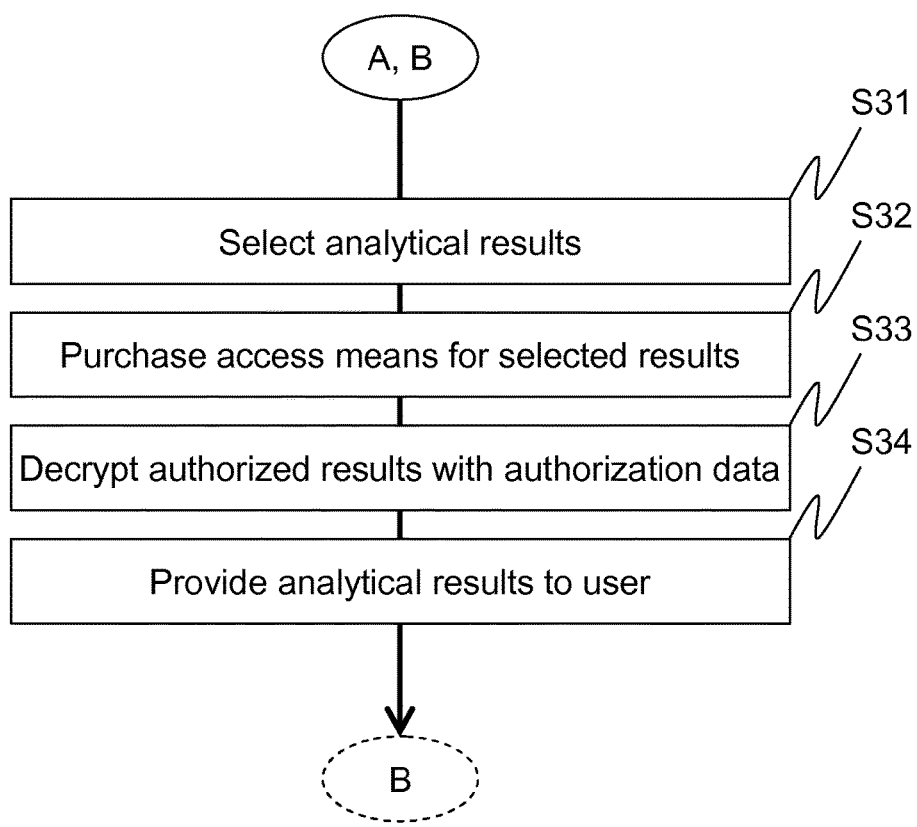
FIG. 5 is a flowchart describing the part of the process in which access to the locked, protected results is enabled for diagnostic tests for which authorization is purchased separately.

A particularly useful variant of step S15 is described in the flow chart in FIG. 3A. A host controller (not shown) in the secure realm of the reader unit communicates with a secure authenticator (not shown) of the assay unit. The host controller of the reader unit sends a challenge to the secure authenticator of the assay unit, and receives a response. The reader unit evaluates if the response from a secure authenticator of an assay unit is authentic. When the assay unit is authentic, the reader unit receives the encrypted rule from the assay unit.

From this point on, the following operations are carried out in the secure realm of the diagnostic system. The decryption algorithm receives the private key and the encrypted rule as input, and produces the matching rule. The conversion algorithm takes raw data and matching rule as inputs to produce the analytical results.

The protection function then encrypts the analytical results using a stored private key (in the secure realm) or a stored public key (not necessarily needing to be in the secure realm). This step corresponds to step S16 in FIG. 3.

The treatment (storage, unlocking, etc.) of the encryption protected analytical results can then be carried out outside the secure realm.

In case the assay unit is a pre-authorized assay unit that has been provided with corresponding authorization data, e.g. in the memory module of the assay unit, the corresponding authorization data are automatically retrieved S21 by the evaluation unit, via the reader unit. Using the authorization data, that part of the encrypted data that corresponds to the authorized analytical results is decrypted, S22, and provided to the user S23. The system is now in state B.

If now the user wishes to access further protected, locked analytical data, or if the assay unit was distributed without pre-authorization, the user selects the desired analytical results S31, and purchases the necessary access means, for example from the manufacturer S32. Upon receipt of the access means, the newly authorized data are decrypted/unlocked S33, and the corresponding analytical results are provided to the user S34.

Figure 6:
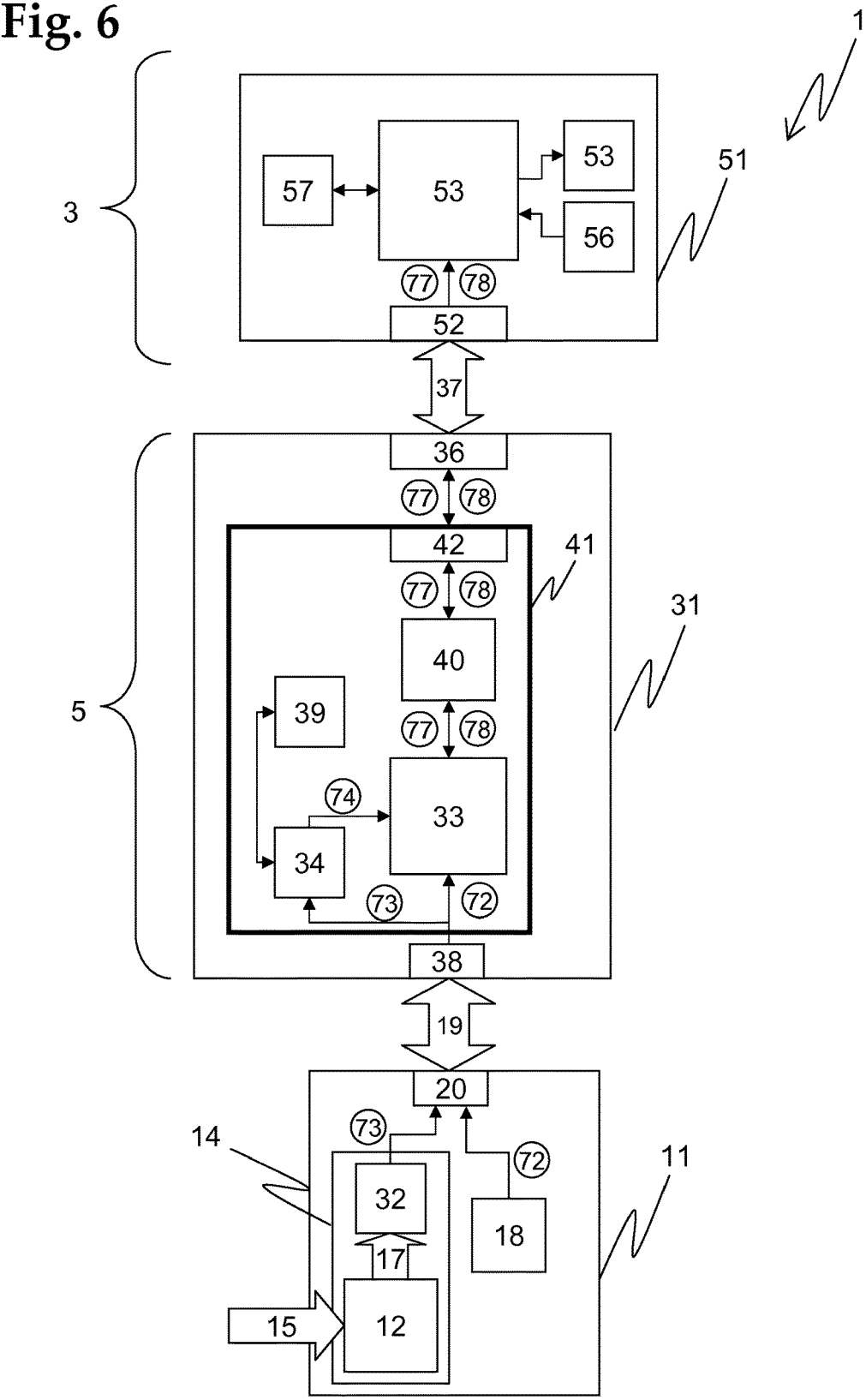
FIG. 6 is a schematic view of another advantageous embodiment of a diagnostic system according to the invention.

Another advantageous embodiment of a diagnostic system 1 according to the invention with assay unit 11, reader unit 31, and evaluation unit 51 is shown in FIG. 6. The system differs from the one in FIG. 1 in that both test module 12 and sensor module 32 are part of the assay unit 11, and are realized in the form of an integrated module 14. The test raw data 73 are provided to the reader unit 31 via the data connection 19, together with the additional data 72.

Figure 7:
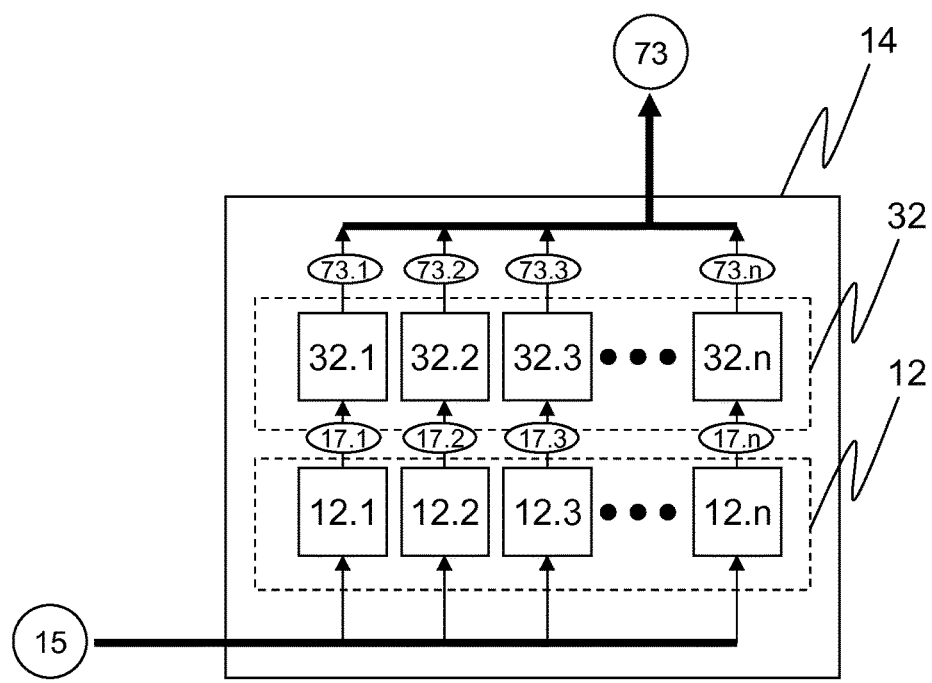
FIG. 7 is a schematic view of the read-out of test result data in the embodiment of a diagnostic system as shown in FIG. 6.

The integrated test and sensor module 14 is schematically shown in FIG. 7. This is the typical case of an analytical device in which the diagnostic test elements and the sensor elements measuring the resulting signal are deeply integrated.

In the tamper-proof protection module 41 of the reader unit 31, the test raw data 73 are processed by data processing unit 34 to analytical result data 74. Said analytical data 74 are then provided to the encryption module 33, where they are locked by encryption, and stored in a memory module 40. The evaluation unit can then read the encrypted data 77 and plain-text data 78 from the memory module 40, via output interface 42 of the protection module 41. The memory module 40 offers the advantage that the activities of the encryption module 33 and the evaluation unit can be decoupled. The memory module may for example be realized as a non-volatile flash memory, in which the encryption module stores the data 77, 78. The evaluation unit may then access said data at any time in the future. Thus the reader unit can read and encrypt the data of the assay unit without yet being operationally coupled to the evaluation unit, and may even read, lock, and store the results of several different assay units. The evaluation unit has then only to be coupled to the reader unit for a short period that is sufficient to download the data 77, 78 from the memory module 40.

Instead of establishing a direct live data connection between reader unit and evaluation unit, it is also possible to realize the memory module 40 in the form of a releasably mounted flash memory device, such as an SD card, a USB memory stick, or the like. After writing the data on the memory device 40, it is disconnected from the reader unit by the user, and subsequently connected to the evaluation device, where the data are read. However, such an approach is nevertheless a data connection 37 in the sense of the invention. In order to ensure data protection, in such an embodiment no data should be stored in the memory that should remain inside the protection module, such as e.g the unencrypted analytical results.

Figure 8:
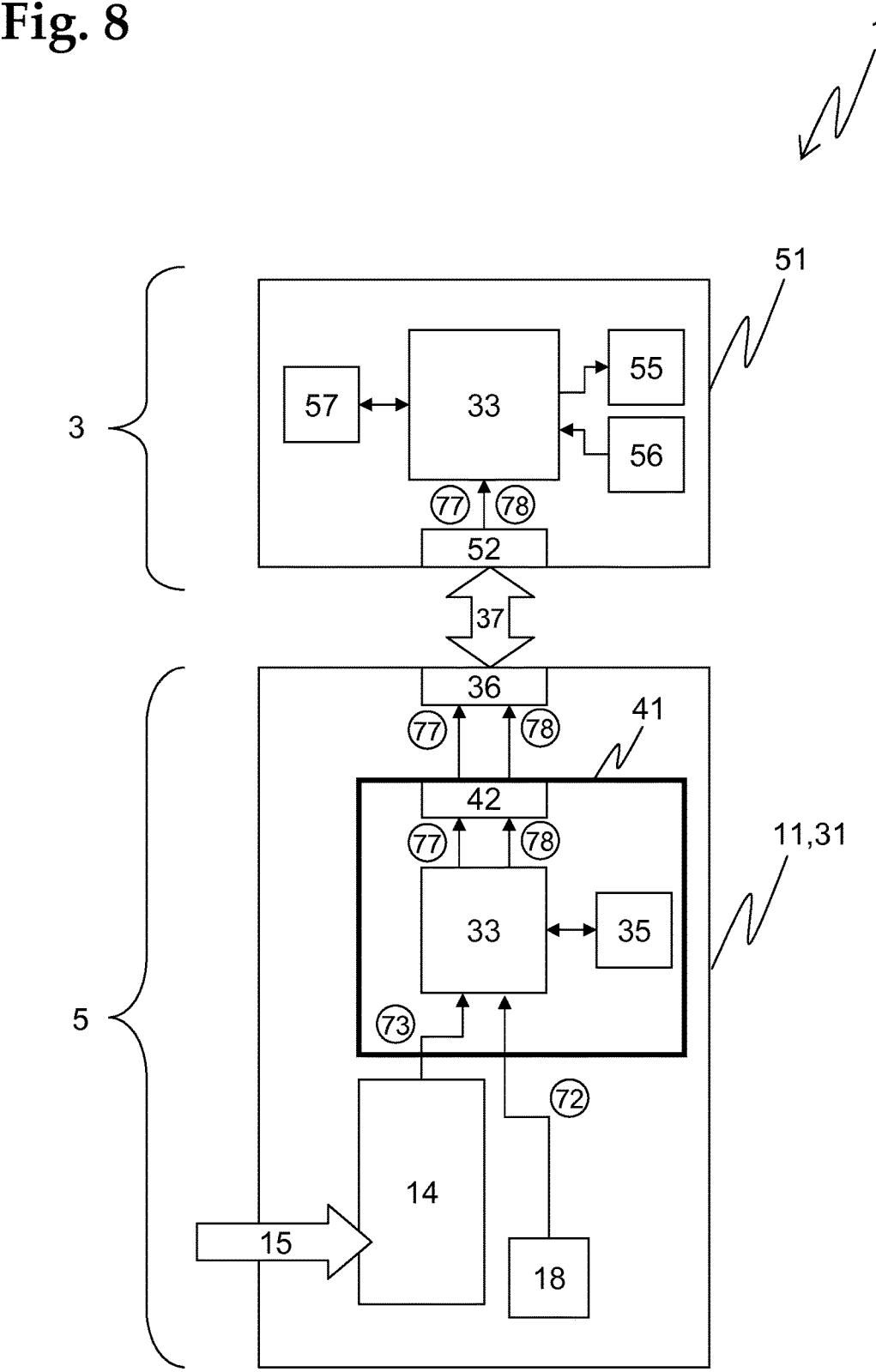
FIG. 8 is a schematic view of a further advantageous embodiment of a diagnostic system according to the invention, in which assay unit and reader unit are realized as a combined device.

Another advantageous variant of a diagnostic system is shown in FIG. 8, in which the assay unit 11 and the reader unit 31 are realized as a single integrated diagnostic device. An integrated test/sensor module 14 carries out the diagnostic tests on the sample 15, and provides test raw data 73 to the encryption module 33 of the protection module 41, which encrypts the data. Encrypted data 77 as well plain-text data 78 can be temporarily stored in memory module 35 of encryption module 33. Locked data 77 and further data 78 can be requested by the evaluation unit 51, via output interface 42.

The shown embodiment is particularly advantageous for more complex assay units, in which the additional costs for the electronic elements 33, 35, 36 of the reader unit part are not relevant in regard to the overall manufacturing costs.

Figure 9:
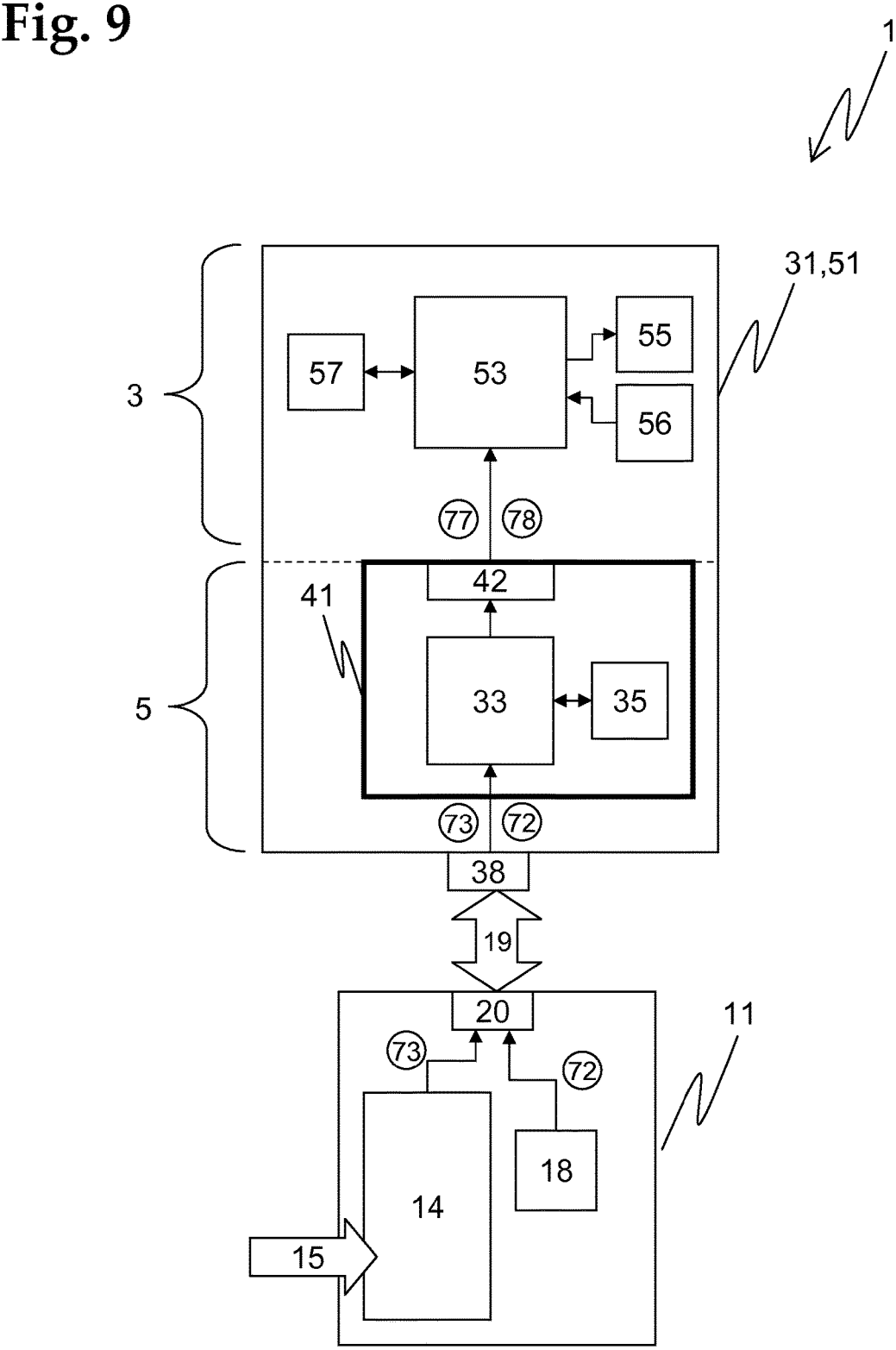
FIG. 9 is a schematic view of yet another advantageous embodiment of a diagnostic system according to the invention, in which evaluation unit and reader unit are realized as a combined device.

Another variant of a diagnostic system 1 according to the invention is shown in FIG. 9, having a reader unit 31 and an evaluation unit 51 that are combined in one single device. The shown embodiment is particularly advantageous as a compact standalone device.

The shown assay unit 11 is the same as it has been shown in FIG. 6. The elements of reader unit and evaluation unit, and their interactions, are similar to previously discussed embodiments. The single device in FIG. 9 comprises both a secure realm 5 and a user realm 3, wherein any data present in the secure realm, namely in the tamper-proof protection module 41, are not accessible from outside 5, except when they are provided by the reader unit 31 on an internal output interface 42 of the protection module 41.

Figure 10:
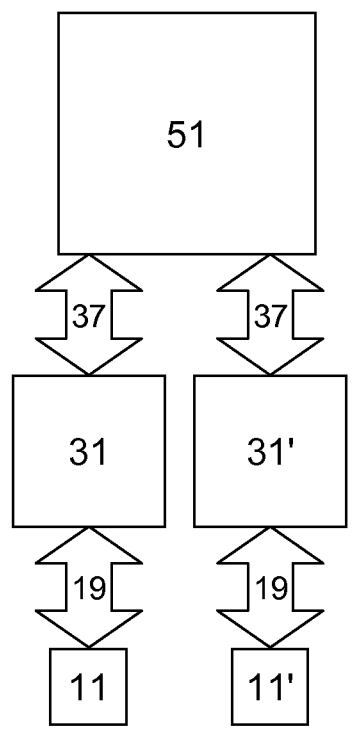
FIG. 10 schematically shows (a) a diagnostic system according to the invention with two reader units sharing one evaluation unit, and (b) a diagnostic system according to the invention with a reader unit capable of being operationally coupled with two assay units at the same time.
Figure 10:
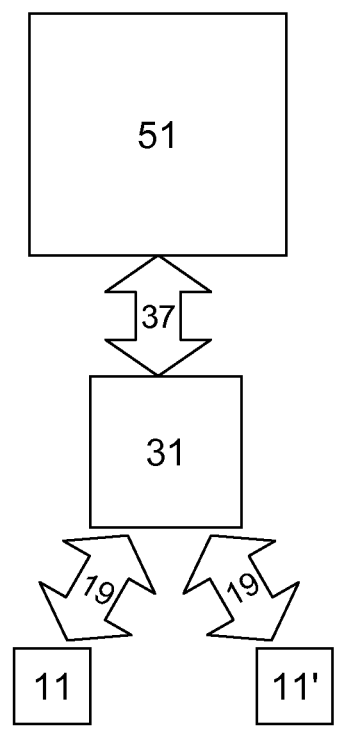

In the embodiments shown so far, one evaluation unit has been operationally coupled to one reader unit, which itself has been operationally coupled to one assay unit. However, the invention does also encompass other combinations. For example may a diagnostic system, comprise two or more reader units 31, 31' that are operationally coupled to one common evaluation unit 51, as schematically shown in FIG. 10(*a*). Such an embodiment allows an easy and cost efficient upscale of a diagnostic system. Furthermore it is possible to use different types of reader units, for example for a specific type of assay unit type, without the need on an additional evaluation unit.

Similarly it is possible to provide a reader unit 31 with means for operationally coupling with more than one assay unit 11, 11' at the same time, as for example depicted in FIG. 10(*b*). Such a reader unit thus allows the parallel operation or read-out of more than one assay unit, which increases the throughput. Alternatively the reader unit may be provided with coupling means for different types of assay units.

Figure 11:
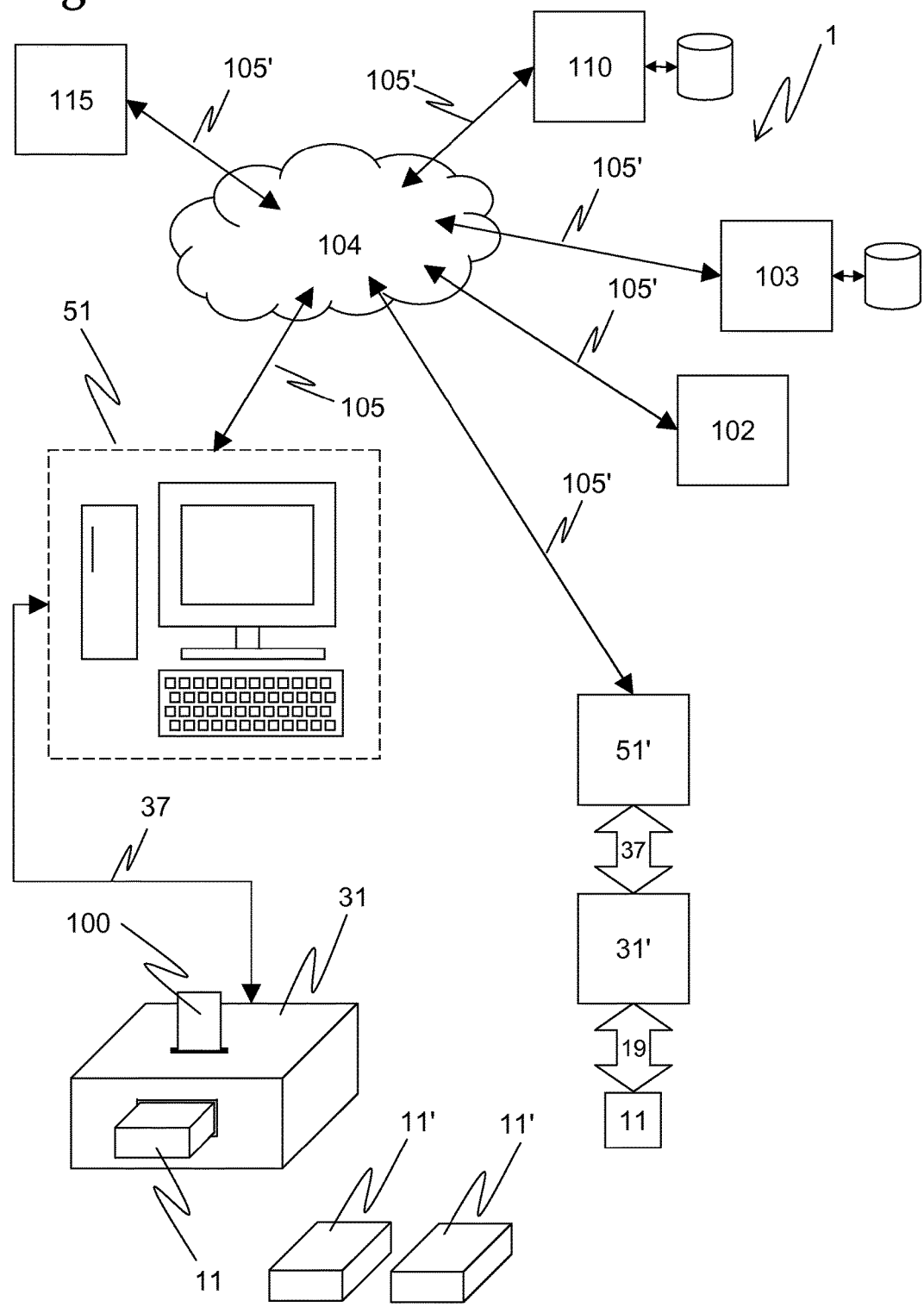
FIG. 11 is a schematic view of a diagnostic system with a remote authorization server and other entities communicating over a generic communication network.

A particularly advantageous variant of a diagnostic system 1 according to the invention is schematically depicted in FIG. 11. The shown exemplary embodiment of a reader unit 31 for use in a diagnostic system according to the invention comprises a first slot on a side wall of the casing in which assay units can be releasably mounted. In addition, a second slot is provided on the cover, in which authorization units can be releasably inserted. In the figure, an assay unit 11 is shown inserted in the first slot, and an authorization unit in the form of a smart card is inserted in the second slot. Two additional consumable assay units 11' are ready for later use.

The reader unit 31 is connected via a data connection 37 (e.g. a USB connection or a WLAN connection) with an evaluation unit 51. The evaluation unit 51 in the given example is a standard computer device, namely a desktop computer with display and keyboard, on which suitable programs can be carried out, in order to fulfil the functions of the evaluation unit.

The different approaches for the function of the authorization unit have been discussed further above. The authorization smart card 100 may for example comprise credit units, which allows to access the results of certain diagnostic tests, depending on the amount of credit units assigned to said tests. Alternatively it may comprise authorization data that allow a user to access specific, pre-authorized test results. Instead of being connected with the reader unit, the authorization means may also be connected with the evaluation unit.

The evaluation unit 51 is connected 105 to a generic communication network 104. The term communication network has to be understood to include any link that allows data communication from one point to another, be it via a dedicated wire based or wireless link, the internet, a mobile network, a secure channel such as a VPN connection, etc. The link to the communication network may be realized for example by phone line, DSL or cable modem, cellular link, wireless link, Ethernet, etc.

A remote authorization server 110 is also connected 105' to the communication network 104. The functions of the remote authorization server have been discussed further above. For example may the evaluation device 51 communicate encrypted locking keys to the authorization server 110, in order to receive back the decrypted locking keys, or parts of them, depending on the authorization level of the evaluation unit.

A remote payment clearing server 115 connected to the communication network 104 allows a user, or his evaluation unit, respectively, to purchase authorization means. Such authorization means (credit units, authorization data, etc.) may then enable the user to access additional analytical results.

An remote access device 102, and a remote storage server 103 may also communicate with the evaluation device 51, in order to remotely access or store the analytical results.

The remote authorization server 110, remote payment clearing server 115, remote access device 102, and remote storage server 103 can operate with more than one evaluation unit. In the figure, a second schematic evaluation unit 51' is connected to the network 104, which may be under control of a different user.

An illustrative graphical user interface (GUI) for selecting, purchasing and viewing analytical results is shown in FIG. 12. Such a GUI may be realized by software running on a computer device acting as the evaluation unit, or on a display of a dedicated evaluation unit, or even on a remote access device.

The interface may include items identifying different types of analytical results (e.g. small molecules, proteins, DNA, cells, viruses, bacteria). A user may insert a variety of assays with different specifications and analytical capabilities into a reader unit, in order to measure and import a multitude of locked analytical results into a database.

A user may then select one or more analytical results to purchase or view. For example, a user may select analytical results using check boxes, or other approaches. Filled check boxes may correspond to analytical results for which access authorization has been purchased previously, or for which access which provided bundled with the assay unit. Check marks may correspond to analytical results selected to be purchased. Potentially available analytical results may be grouped, for example as application panels (e.g. Cardiac Markers, Virology, Inflammation Markers).

When the check box of a group is checked or filled, the checkmark state may be inherited by all underlying analytical results. Individual analytical results may be accessed and selected by expanding the application panel and checking the corresponding check box (ref. "C-reactive protein"). Such sub-selection may be indicated as a dashed application panel check box (ref. "Inflammation Markers").

Application panels and analytical results that are not available in the database, or from the assay unit capabilities may be indicated as disabled (grayed out) (ref. "Drug Screening").

A user may select the "back" arrow to return to a previous interface. The "order" arrow allows to proceed to the order interface.

In the shown embodiment, the interface may emphasise certain analytical results. These analytical results may be indicative of an underlying health condition. For example, such emphasis is shown to "Cardiac Markers" and "Hematology", because the concentration of the analytes may be outside the healthy reference range. The unusual concentration of these analytes may indicate an underlying health condition or disease. For example, emphasis is shown on the cardiac marker "Troponin T", because its concentration may be above the healthy reference range, indicating the patient may have experienced a heart injury.

Such a system may be especially useful to quickly scan through multiple analytes, to check the overall health of a patient, and to identify potential health problems. The system may alert the user of any abnormal diagnostics results. A user may decide to purchase or view these emphasized analytical results.

Figure 13:
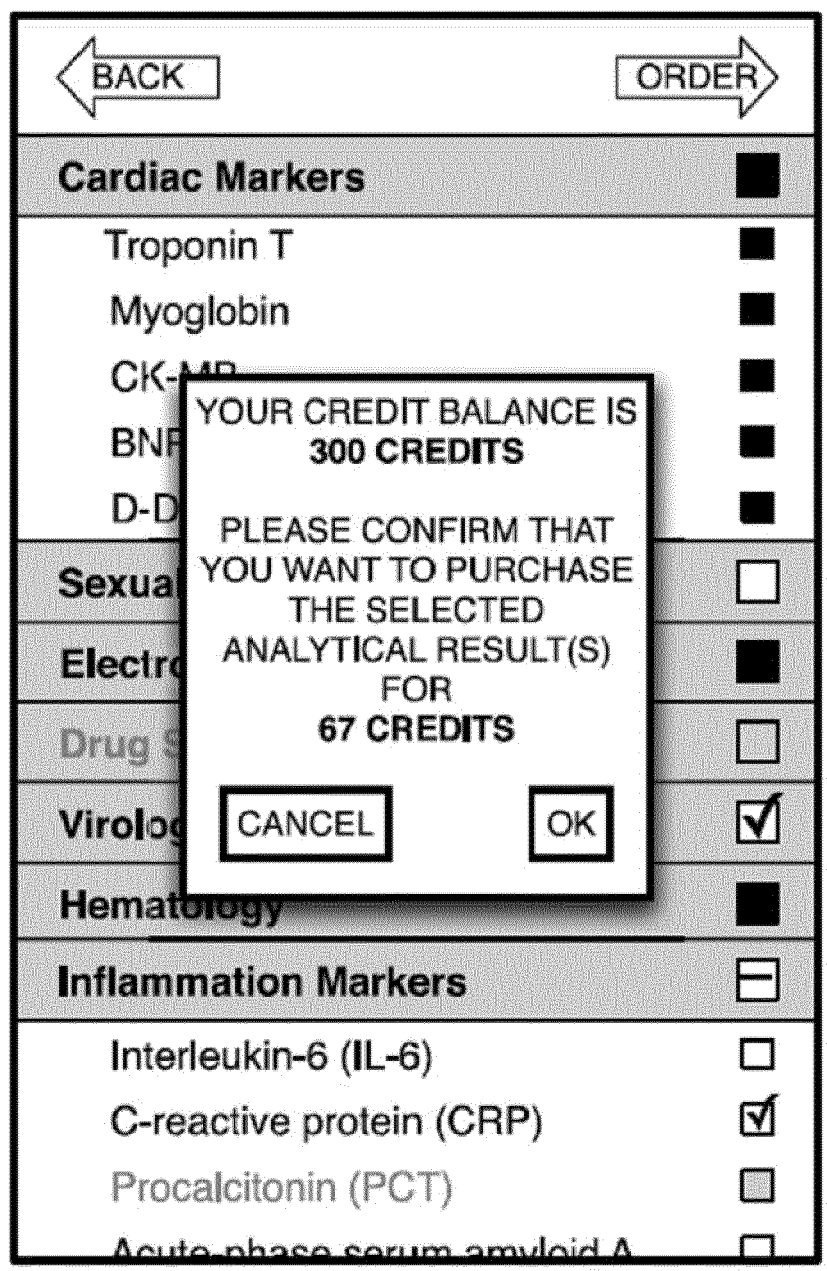
FIG. 13 is a schematic view of a illustrative interface for confirming the purchase of analytical results.
Figure 14:
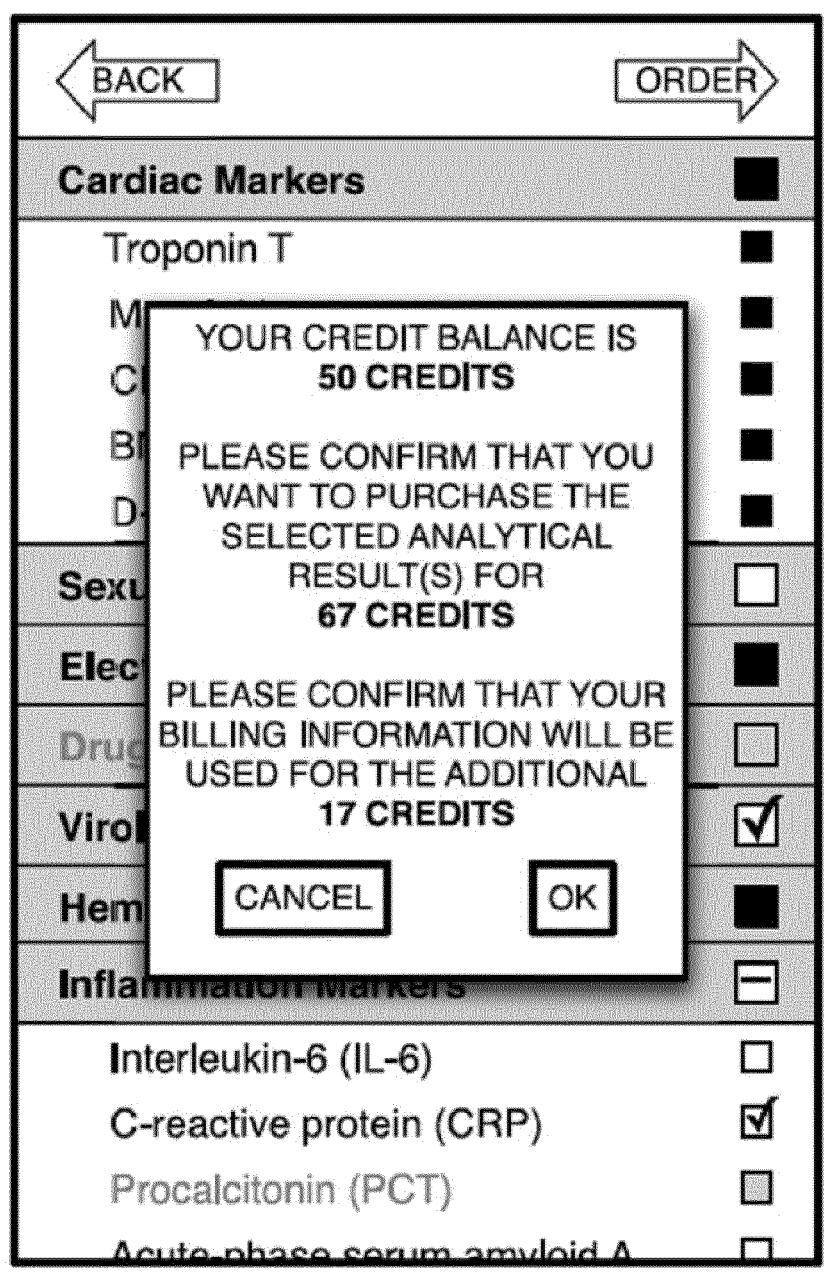
FIG. 14 is a schematic view of another illustrative interface for confirming the purchase of analytical results.

FIGS. 13 and 14 are schematic views of an illustrative interface for confirming the purchase of analytical results. A user may purchase the selected analytical results using an electronic purchase order, where credit units may come from the user credit balance on a reader unit or evaluation unit, or from credit units that are bundled on an assay unit, or by accessing user invoice information and communicating with a remote payment server.

FIG. 13 describes the situation where the user credit balance is sufficient to purchase access to the selected analytical results. A confirmation interface may appear, in the given example a pop-up window arranged over the menu as previously shown in FIG. 12, to inform the user about his current user credit balance, the price in credit units of the selected analytical results, and to enable the user to confirm or cancel the purchase of analytical results.

FIG. 14 describes the case where the user credit balance is not sufficient to purchase the selected analytical results. A confirmation interface in the form of a pop-up window informs the user about his current user credit balance, the price in credits of the selected analytical results, and the amount to be billed using the user's billing information. The user may then confirm or cancel the purchasing of analytical results, by pressing the corresponding buttons.

Figure 15:
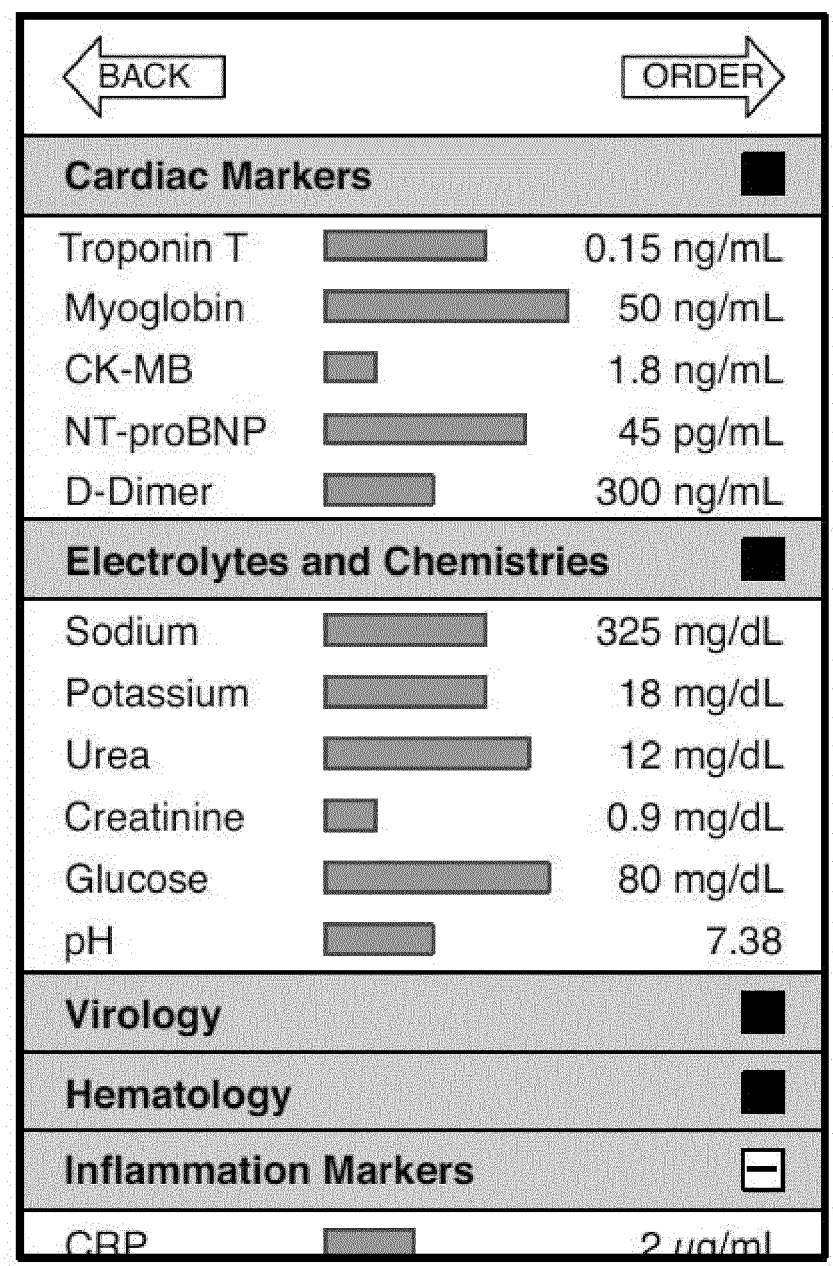
FIG. 15 is a schematic view of an illustrative interface for displaying analytical results.

FIG. 15 is a schematic view of an illustrative interface for displaying the purchased analytical results. In this example, only the purchased application panels and underlying analytical results are displayed. Additionally, there may be many other results which may be incorporated in such an interface, such as comparative results of other users, or analytical results which were not yet purchased, or which are unavailable, etc. Application panels may be accessed to display individual analytical results. Information such as reference concentration range and analyte concentration may be displayed and additional information may be accessed. Filled application panel check boxes may indicate that all corresponding analytical results have been purchased. Dashed application panel check boxes may indicate that only part of the corresponding analytical results have been purchased.

FIG. 16 is a schematic view of an illustrative interface for a database of analytical result data and the ability to retrospectively select, purchase or view analytical results. Analytical results may be stored locally on an evaluation unit, or on a remote storage server. The display may show a database of result data that may be organized according to several criteria such as chip (assay unit) information (e.g. chip identification, chip specifications, chip lot number, chip bundled analytical results, etc.), diagnostic test information (e.g. test date, test time, etc.), user information (e.g. user identification, user name, etc.), and sensor information (e.g. analytical panels, sensor raw data, sensor analytical results, etc.).

A user may sort analytical test data by a variety of criteria, such as by column name or using search filter terms. Test data may be selected to further viewing or purchasing of analytical results. Test data may be stored for every test even when the analytical results were not purchased or viewed at the time when the test was done. Therefore, a user may select test data from previous tests at any time, and may retrospectively purchase or view analytical results.

Figure 17:
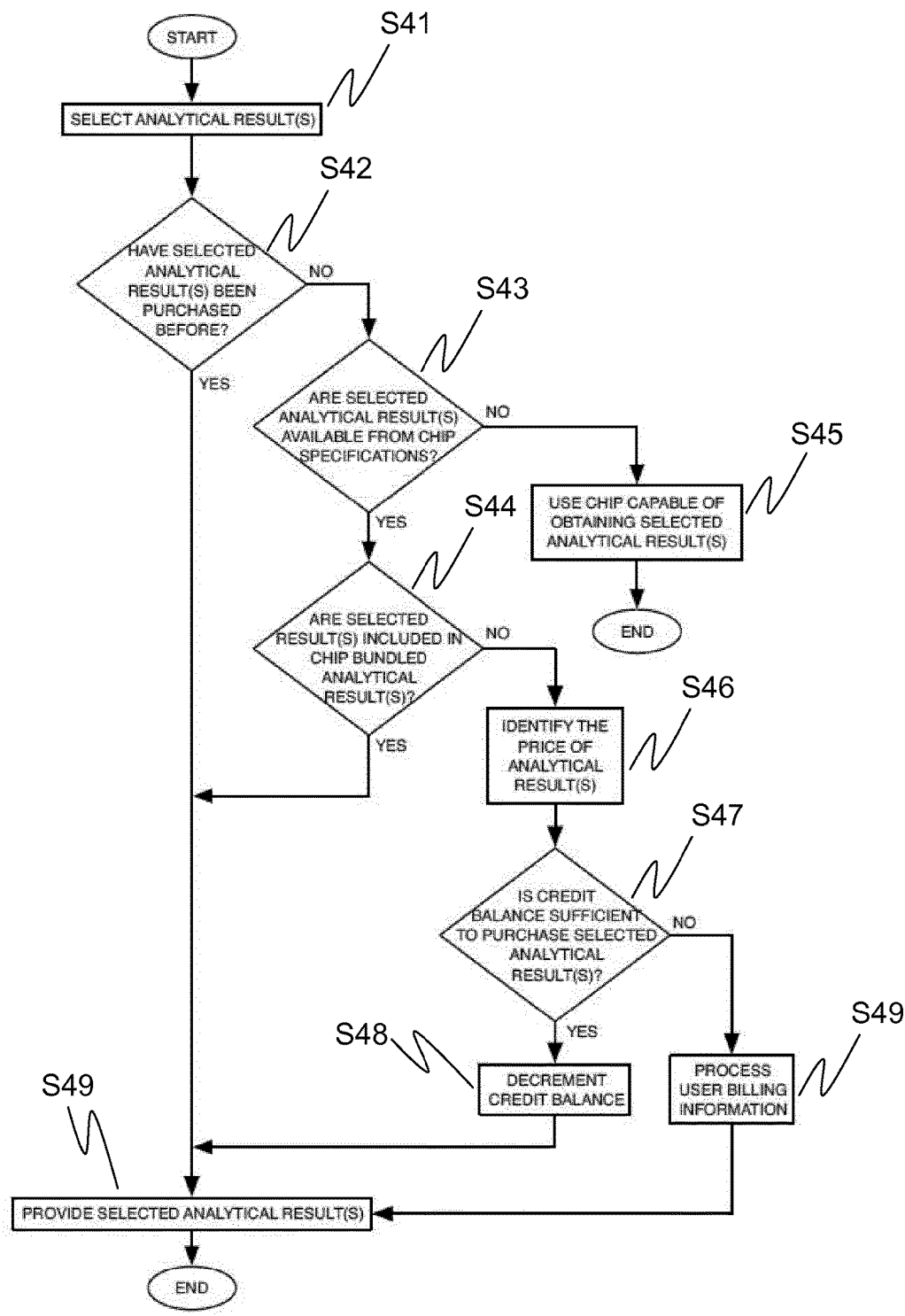
FIG. 17 is a flowchart describing the procedure of securing, purchasing and viewing analytical results.

FIG. 17 is a flowchart describing a procedure of securing, purchasing and viewing analytical results with a diagnostic system according to the invention. The analytical results have been measured, locked, and stored on the reader unit, evaluation unit, or assay unit as explained above.

A user may select analytical results to purchase or view S41. The reader unit or evaluation may check if the analytical results have been purchased before S42, for example by reading a registry.

If yes, the reader unit or evaluation unit may provide the analytical results to the user for viewing S49.

If no, the reader unit or evaluation unit may determine S43 whether the analytical results are available from the assay unit specifications; i.e. the assay unit, for example a diagnostic chip, has the capabilities to detect the analytes.

If no, the user may be prompted S45 to use another type of assay unit that is capable of obtaining the selected analytical results. The process may then start again with step S41.

If yes, the reader unit or evaluation unit may determine S44 whether the selected analytical results are included in the analytical results that are per-enabled fro the assay unit, thus the results for which the authorization means have been provided bundled with the assay unit.

If yes, the analytical results may be provided to the user for viewing, S49.

If no, the reader unit or evaluation unit may identify the price of the analytical results, S46.

This may be done using a local database of prices, or by connecting to a remote server with a database of prices. The reader unit or evaluation unit may verify S47 if the user credit balance is sufficient to purchase the selected analytical results.

If yes, the user credit balance may be decremented S48, and the analytical results may be provided to the user, S49.

If no, the reader unit or evaluation unit may process S49 the user invoice information, and provide the selected analytical results to the user, S49.

Figure 18:
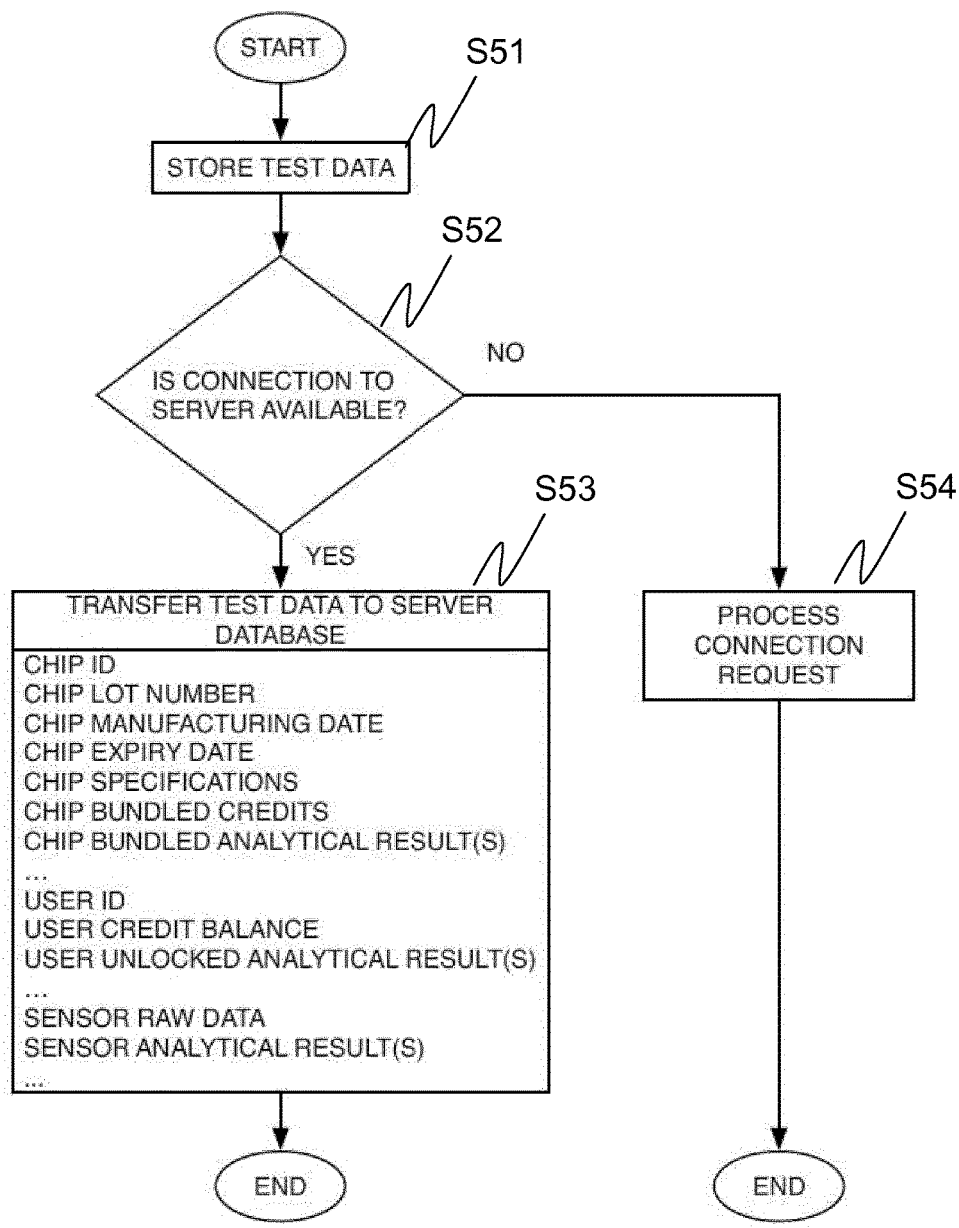
FIG. 18 is a flowchart describing the procedure of transferring test data to a server.

FIG. 18 is a flowchart describing a procedure of transferring analytical result data to a remote storage server. The locked analytical result data and further data may be stored S51 on a reader unit, evaluation unit, or diagnostics chips as shown above.

The system will then check S52 if a connection to the remote server is available.

If yes, the data may be transferred S53 to the remote server database. The data may contain information such as chip information, user information, and sensor information, etc.

If no, the reader unit may process a connection request S54. After establishing the connection, data may be transferred to the server using standard secure communication protocols.

Figure 19:
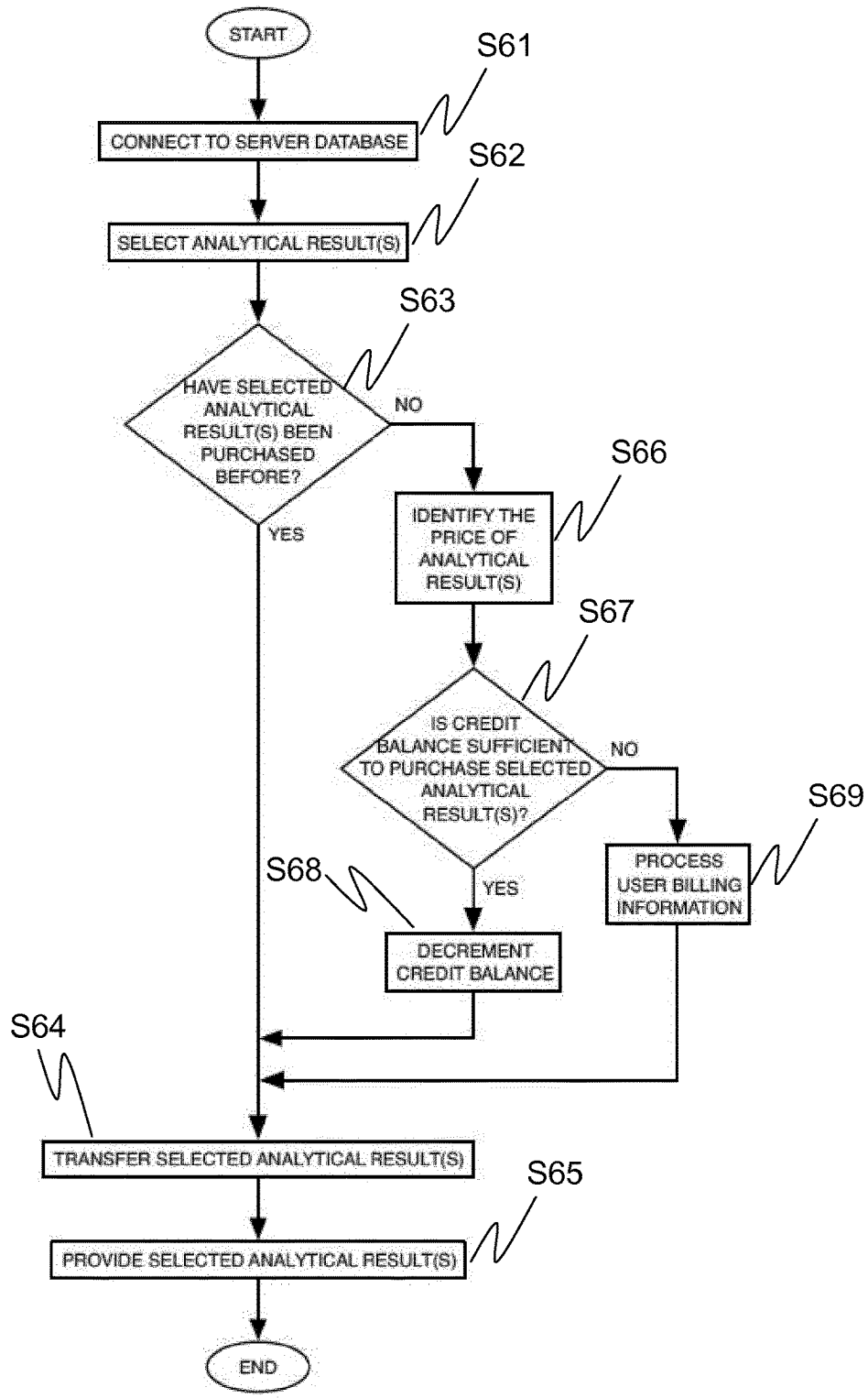
FIG. 19 is a flowchart describing the procedure of purchasing or viewing analytical results stored in a server database.

FIG. 19 is a flowchart describing a procedure of purchasing or viewing analytical results stored in a database of a remote storage server. A reader unit or evaluation unit may connect S61 to a remote storage server. A user may then select S62 analytical results to purchase or view. The server may verify if the selected analytical results have been purchased before S63.

If yes, the analytical results may be transferred S64 to the reader unit or evaluation unit, and the analytical results may be provided S65 to the user.

If no, the server may identify S66 the price of the analytical results. The server may then verify S67 if the user credit balance is sufficient to purchase the selected analytical results.

If yes, the user credit balance may be decremented accordingly S68. If no, the user invoice information may be processed, S69. The analytical results may then be transferred S64 to the reader unit or evaluation unit, and provided S65 to the user.

It is readily apparent to one of ordinary skill in the art that changing the order of the steps in the above flow charts will result in purchasing and viewing of secure analytical results. Thus, changing the order of the procedures for selecting, transferring, purchasing and viewing test data and analytical results are within the scope of the invention.

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

LIST OF REFERENCE NUMERALS 1 diagnostic system
3 user, user realm
5 secure realm
7 diagnostic device
11, 11' assay unit
12 test module
12.1, 12.2, . . . test element of a single diagnostic test
13 diagnostic test
14 integrated test and sensor module
15 physiological sample
17 diagnostic test signal
17.1, 17.2, . . . test signal of a single diagnostic test
18 memory module
19 data connection
20 data interface
25 data carrier
31 reader unit
32 sensor module
32.1, 32.2, . . . sensor element
33 encryption module
34 data processing module
35 memory module
36 first data interface
37 data connection
38 second data interface
39 memory module
40 memory module
41 protection module
42 output interface
51, 51' evaluation unit
52 data interface
53 data processing module, processor
55 data output module
56 data input module
57 memory module
72 additional data
73 test raw data, complete data set of analytical results
73.1, 73.2, . . . raw data of a single diagnostic test
73a authorized test raw data, authorized subset of the complete data set of analytical results
74 analytical result data, entirety of analytical results, complete data set of analytical results
74a authorized analytical results, authorized subset of the complete data set of analytical results
75 locking key data
75.1, 75.2, . . . locking key
77 encrypted data, encrypted complete data set of analytical results
77.1, 77.2, . . . subset of encrypted data
77a accessible encrypted data
78 further data
79 authorization key data
79.1, 79.2, . . . authorization key
80, 80' decrypted data
80.1, 80.2, . . . subset of decrypted data
82 second level key data
82.1, 82.2, . . . second level key
84 encrypted locking key data
86 privacy key data
100 authorization unit
102 remote access device
103 remote storage server
105, 105' connection to communication network
104 communication network
110 remote authorization server
115 payment clearing server

The invention claimed is:

1. A reader unit (31), configured to be operationally coupled with a multiplexed diagnostic test assay unit (11) configured to carry out in parallel multiple diagnostic tests on one or more physiological samples, and wherein the reader unit is configured to obtain test raw data (73) of diagnostic tests performed on the assay unit operationally coupled with the reader unit, the reader unit comprising:
a data protection module (41) that is configured to obtain and temporarily store the test raw data, to convert said test raw data into analytical result data (74), to encrypt (33) said analytical result data with locking key data (75) to encrypted data (77), and to selectively provide parts or all of said encrypted data on an output interface (42); wherein the protection module is a tamper-proof module that is configured to prevent access to data (73, 74) stored in the module;
a sensor module including a plurality of sensor elements each configured to provide a raw data output from a corresponding test element of the multiplexed diagnostic test assay unit; and
wherein the data protection module comprises an encryption module configured to parse and store subsets of the encrypted data, which together form an encrypted complete data set of the analytical result data.

2. The reader unit according to claim 1, wherein the protection module (41) is configured to encrypt the locking key data (75) with second level key data (82) to encrypted locking key data (84), and to provide said encrypted locking key data on the output interface (42).

3. A diagnostic device, comprising: a reader unit (31) according to claim 1, and a multiplexed diagnostic test assay unit (11) configured to carry out in parallel multiple diagnostic tests on one or more physiological samples, the assay unit and the reader unit being permanently or releasably operationally coupled to each other, and the reader unit being configured to obtain test raw data (73) of diagnostic tests performed on the assay unit; and/or an evaluation unit (51), the evaluation unit and the reader unit being permanently or releasably operationally coupled to each other (37, 28, 52), and the evaluation unit being configured to receive data (77, 78, 84) from the reader unit, to selectively decrypt parts or all of said data, using authorization key data (79), and to use the decrypted output data for obtaining analytical result data (74).

4. A diagnostic system (1), comprising: one or more reader units (31, 31') according to claim 1; one or more multiplexed diagnostic test assay units (11, 11') configured to carry out in parallel multiple diagnostic tests on one or more physiological samples, the assay units being configured to be operationally coupled to the reader units, and the reader units being configured to obtain test raw data (73) of diagnostic tests performed on the assay units; and one or more evaluation units (51), configured to be operationally coupled to the reader units, to receive data (77, 78, 84) from the reader units, to selectively decrypt parts or all of said data, using authorization key data (79), and to use the decrypted output data for obtaining analytical result data (74).

5. The diagnostic system according to claim 4, wherein an evaluation unit (51) comprises a data processing module (53) that is configured to decrypt encrypted data (77, 84).

6. The diagnostic system according to claim 4, further comprising one or more authorization units (100) operationally coupled to an evaluation unit (51), and/or one or more remote authorization servers (110) connected to the evaluation unit via a communication network (104), the authorization units and/or remote authorization servers being configured to provide, upon fulfillment of certain conditions, the authorization key data (79) to the evaluation unit; or the authorization units and/or remote authorization servers being configured to receive encrypted data (77, 84) from the evaluation unit, to decrypt parts or all of the encrypted data upon fulfillment of certain conditions, and to provide the decrypted data (80, 80') to the evaluation unit.

7. A diagnostic kit, comprising: one or more multiplexed diagnostic test assay units (11, 11') with a test module (12) configured to carry out in parallel multiple diagnostic tests on one or more physiological samples, and a reader unit (31) according to claim 1.

8. A method for controlling access of a user (3) to analytical results (73, 74) of a multiplexed diagnostic test assay unit (11) on a reader unit according to claim 1, comprising the steps:
   a) providing the multiplexed diagnostic test assay unit (11) that is configured to carry out in parallel multiple diagnostic tests (13) on one or more physiological samples (15);
   b) reading out from said assay unit a complete data set (73, 74) of analytical results of said multiple diagnostic tests;
   c) encrypting the complete data set of analytical results with locking key data (75) and storing the encrypted results;
   d) providing the encrypted complete data set (77) of analytical results to the user; and
   e) providing the user with authorization means that enable the user to get selective access to parts or all of the complete data set of analytical results as present in the encrypted complete data set of analytical results, but not to the other part of the complete data set of analytical results.

9. The method according to claim 8, wherein the authorization means are authorization key data (79) that allow to decrypt certain parts of the encrypted complete data set (77) of analytical results, such that the decrypted data (80) correspond to the certain authorized subset (73a, 74a) of the complete data set (73, 74) of analytical results.

10. The method according to claim 8, wherein the authorization means are authorization data that enable the user to receive authorization key data (79) from an authorization unit (100), or from a remote authorization server (110), wherein the authorization key data allow to decrypt certain parts of the encrypted complete data set (77) of analytical results, such that the decrypted data (80) correspond to the certain authorized subset (73a, 74a) of the complete data set (73, 74) of analytical results.

11. The method according to claim 8, wherein in step c) different subsets (73.1, 73.2, . . . , 74.1, 74.2, . . .) of the complete data set (73, 74) of analytical results are encrypted with different locking keys (75.1, 75.2, . . .), which together form the locking key data (75), to different subsets of encrypted data (77.1, 77.2), which together form the encrypted complete data set (77) of analytical results.

12. The method according to claim 11, wherein encryption in step c) takes place with an asymmetric encryption algorithm, and that the locking keys are public keys (75.1, 75.2, . . .) for the asymmetric encryption algorithm.

13. The method according to claim 12, wherein the authorization means comprise private keys of the asymmetric encryption algorithm, which together form the authorization key data, wherein said private keys allow to decrypt those subsets of the encrypted complete data set of analytical results, of which the decrypted data subsets (80.1, 80.2, . . .) correspond to the certain authorized subset (73a, 74a) of the complete data set (73, 74) of analytical results.

14. The method according to claim 11, wherein encryption in step c) takes place with a symmetric encryption algorithm, and that the locking keys are secret keys (75.1, 75.2, . . .) for the symmetric encryption algorithm.

15. The method according to claim 14, wherein the authorization means comprise certain keys (79.1, 79.2, . . .) of the locking key data (75), which together form the authorization key data (79), wherein said certain keys (79.1, 79.2, . . .) allow to decrypt those subsets (77.1, 77.2, . . .) of the encrypted complete data set (77) of analytical results of which the decrypted data subsets (80.1, 80.2, . . .) correspond to the certain authorized subset (73a, 74a) of the complete data set (73, 74) of analytical results.

16. The method according to claim 14, wherein after step c) the locking key data (75) are encrypted with an asymmetric encryption algorithm, using one or more public keys (82.1, 82.2, . . .) for the asymmetric encryption algorithm, which together form second level key data (82), to encrypted locking key data (84).

17. The method according to claim 8, wherein the encrypted complete data set (77) of analytical results is provided to an authorization unit (100), or to a remote authorization server (110), and that the authorization means are authorization data that enable the user to command the authorization unit, or the remote authorization server, to decrypt certain parts of the encrypted data, such that the decrypted data (80) correspond to the certain authorized subset (73a, 74a) of the complete data set (73, 74) of analytical results, and to provide the decrypted data to the user.

18. The method according to claim 17, wherein prior to encryption, the different subsets of the data set are encrypted with privacy key data (86), which are provided to the user.

19. The method according to claim 8, further comprising:
   providing the user with a first authorization means that enables the user to a first part of the encrypted complete data set of analytical results, but not to a second part of the encrypted complete data set of analytical results;
   after providing the user with a first authorization means, receiving a request from the user for access to the second part of the encrypted complete data set of analytical results; and
   providing the user, in a further step, with a second authorization means that enables the user to the second part of the encrypted complete data set of analytical results.

* * * * *